US010759826B2

(12) United States Patent
Kotora et al.

(10) Patent No.: US 10,759,826 B2
(45) Date of Patent: Sep. 1, 2020

(54) 15β-SUBSTITUTED ESTRONE DERIVATIVES AS SELECTIVE INHIBITORS OF 17β-HYDROXYSTEROID-DEHYDROGENASES, METHOD OF PREPARATION AND USE THEREOF

(71) Applicants: USTAV ORGANICKE CHEMIE A BIOCHEMIE AV CR, V.V.I., Prague (CZ); USTAV MOLEKULARNI GENETIKY AKADEMIE VED CR, V.V.I., Prague (CZ); UNIVERZITA PALACKEHO V OLOMOUCI, Olomouc (CZ); HELMHOLTZ ZENTRUM MUNCHEN, Neuherberg (DE)

(72) Inventors: Martin Kotora, Prague (CZ); Eva Prchalova, Prague (CZ); Jerzy Adamski, Munich (DE); Gabriele Moeller, Munich (DE); Ondrej Stepanek, Liberec (CZ); Petr Bartunek, Prague (CZ); David Sedlak, Prague (CZ); Marian Hajduch, Moravsky Beroun (CZ); Petr Dzubak, Brodek u Prerova (CZ)

(73) Assignees: USTAV ORGANICKE CHEMIE A BIOCHEMIE AV CR, V.V.I., Prague (CZ); USTAV MOLEKULARNI GENETIKY AKADEMIE VED CR, V.V.I., Prague (CZ); UNIVERZITA PALACKEHO V OLOMOUCI, Olomouci (CZ); HELMHOLTZ ZENTRUM MUNCHEN, Neuherberg (DE)

( * ) Notice: Subject to any disclaimer, the term of this patent is extended or adjusted under 35 U.S.C. 154(b) by 0 days.

(21) Appl. No.: 16/305,829

(22) PCT Filed: Jun. 7, 2017

(86) PCT No.: PCT/CZ2017/050022
§ 371 (c)(1),
(2) Date: Nov. 29, 2018

(87) PCT Pub. No.: WO2017/211330
PCT Pub. Date: Dec. 14, 2017

(65) Prior Publication Data
US 2019/0330258 A1    Oct. 31, 2019

(30) Foreign Application Priority Data
Jun. 7, 2016 (CZ) .................................... 2016-342

(51) Int. Cl.
*A61K 31/566* (2006.01)
*C07J 1/00* (2006.01)

(52) U.S. Cl.
CPC .................................... *C07J 1/0059* (2013.01)

(58) Field of Classification Search
CPC ........................... A61K 31/566; C07J 1/0059
See application file for complete search history.

(56) References Cited

U.S. PATENT DOCUMENTS

| 7,419,972 | B2 | 9/2008 | Hillisch et al. |
| 2005/0192263 | A1 | 9/2005 | Messinger et al. |
| 2006/0281710 | A1 | 12/2006 | Messinger et al. |
| 2008/0146531 | A1 | 6/2008 | Messinger et al. |

FOREIGN PATENT DOCUMENTS

| WO | 9946279 | A2 | 9/1999 |
| WO | 2004085457 | A2 | 10/2004 |
| WO | 2005047303 | A2 | 5/2005 |
| WO | 2006003012 | A1 | 1/2006 |
| WO | 2006003013 | A2 | 1/2006 |
| WO | 2006125800 | A1 | 11/2006 |
| WO | 2008034796 | A2 | 3/2008 |
| WO | 2008065100 | A1 | 6/2008 |
| WO | 2012129673 | A1 | 10/2012 |
| WO | 2013045407 | A1 | 4/2013 |
| WO | 2014009274 | A1 | 1/2014 |
| WO | 2014128108 | A1 | 8/2014 |
| WO | 2014207309 | A1 | 12/2014 |
| WO | 2014207310 | A1 | 12/2014 |
| WO | 2014207311 | A1 | 12/2014 |

OTHER PUBLICATIONS

International Search Report for corresponding PCT application No. PCT/CZ2017/050022, dated Aug. 17, 2017.
Written Opinion for corresponding PCT application No. PCT/CZ2017/050022, dated Dec. 14, 2017.

*Primary Examiner* — Brenda L Coleman
(74) *Attorney, Agent, or Firm* — Notaro, Michalos & Zaccaria P.C.

(57) ABSTRACT

15β-substituted derivatives of estrone of general formula I wherein $R^1$, $R^2$, $R^3$, $R^4$, $R^5$ are independently selected from the group consisting of: $C_1$-$C_4$ alkyl, $C_1$-$C_4$ alkoxy, $C_1$-$C_4$ halogenalkyl, halogen, $COOR^6$ wherein $R^6$ is $C_1$-$C_4$ alkyl; H, OH; optionally, $R^3$, $R^4$ and $R^5$ are each formed by a hydrogen atom, while $R^1$ and $R^2$ together form an aryl group, preferably naphthyl, in which the aromatic ring in position C-15 can be mono-, di-, tri-, tetra- and penta-substituted with substituents $R^1$-$R^5$. Compounds of the invention may be used for diagnosis and possibly also for the treatment of estrogen-dependent diseases.

10 Claims, 4 Drawing Sheets

15β-SUBSTITUTED ESTRONE DERIVATIVES AS SELECTIVE INHIBITORS OF 17β-HYDROXYSTEROID-DEHYDROGENASES, METHOD OF PREPARATION AND USE THEREOF

FIELD OF ART

The present invention involves the preparation and utilization of novel ligands, selectively inhibiting the 17β-hydroxysteroid dehydrogenase enzymes (17βHSD). Compounds which selectively regulate 17βHSD activity may be an effective component of pharmaceutical compositions, particularly compositions useful for the diagnosis and treatment of estrogen-dependent types of diseases. The present invention further relates to their method of preparation and to the use thereof.

BACKGROUND ART

HSD enzymes belong to the group of NADP(H)/NAD(H) dependent oxidoreductases that regulate in the body the conversion of ketosteroids to hydroxysteroids and vice versa in a process called steroidogenesis. 17βHSD allow this oxidation-reduction process at the C-17 position of the steroid skeleton. Reduction of the C-17-oxo group of steroids turns a biologically not very active estrone (E1) into a highly potent 17β-estradiol (E2) as well as 4-androsten-3,17-dione into testosterone (T) and 5α-androstan-3,17-dione into dihydrotestosterone. These 17β-hydroxy forms, unlike 17β-ketosteroids, have a high affinity for the respective receptors and thus have a major influence on numerous processes in the body, especially the proliferation and differentiation of cells. 17βHSD therefore play a key role in the formation of biologically active estrogens and androgens and specific regulation of these enzymes could open the door to new groups of therapeutic and diagnostic agents (Poirier, D. *Current. Med. Chem.* 2003, 10, 453).

At present, 15 isoenzymes of the 17β-HSD family are already described in the literature, with individual types differing significantly from each other by tissue, substrate and cofactor specificity, as well as the distribution in cells.

Overexpression of some 17βHSD isoenzymes, and thus the excessive production of 17β-hydroxysteroids in tissues, correlates with the occurrence of estrogen/androgen-dependent diseases. Selective inhibitors of the individual isoenzymes could advantageously be used to treat such diseases, and the determination of the rate of expression of the respective types of HSD in the affected tissues could then serve as a diagnostic marker of said diseases. This is the reason for the considerable attention that has been devoted to 17βHSD research in recent decades.

The present invention relates to inhibitors of 17βHSD1 and 17βHSD5 isoenzymes. These isozymes are involved in the production of estrogens and androgens in the human body. They affect the progression of numerous hormone-sensitive diseases, particularly breast cancer, prostate cancer, non-small cell lung cancer (NSCLC), squamous cell carcinoma, and others. Elevated E2 levels result in benign anomalies, especially endometriosis, adenomyosis, uterine myomas, and menstrual cycle disorders. A great deal of effort is still dedicated to searching for substances that are capable of influencing the course of such illnesses. This is due either to the absence of an appropriate therapeutic substance or to the disadvantages of existing therapeutic options used in the treatment of hormone-sensitive diseases. These include, in particular, adverse effects, the emergence of resistance in long-term administration, and, last but not least, the frequent relapse of the disease.

17βHSD1 was the first of all isoenzymes to be described by Engel et al. in the 1950s (Ryan, K. J.; Engel, L. L. *Endocrinology* 1953, 52, 287). 17βHSD1 preferentially regulates the reduction of estrone (E1) to estradiol (E2) and is naturally expressed especially in placenta, ovaries, breast tissue, uterus and endometrium. It catalyzes the production of E2 from E1 in the ovaries; and in peripheral tissues, it controls the level and availability of E2 at the pre-receptor level (intrakrine modulation). To a lesser extent, 17βHSD1 also catalyzes the conversion of dehydroepiandrosterone (DHEA) to 5-androsten-3β,17β-diol ($\Delta^5$-diol).

The importance of the E2 sex hormone in the human body is its strong affinity to estrogen receptors (ER), through which it regulates the expression of a number of genes (so-called transcription factor). ER in idle state are usually found in the cytosol in the form of monomers. After binding E2 to ER, the receptor units dimerize, enter the cell nucleus and bind to the DNA sequence called the estrogen response element (ERE). After the E2-2ER complex is bound to ERE, a cascade of processes is activated leading to cell proliferation and differentiation. This multiplication of cells can be both physiological and pathological, leading to malignant proliferation (Ciocca, D. R.; Fanelli, M. A. *Trends Endocrinol Metab.* 1997, 8, 313).

It follows from the above that proliferation and differentiation of cells caused by estrogens can be regulated by influencing the metabolism of E2. One possibility is to avoid the binding of E2 to the active site of ER, another possibility is blocking the synthesis of E2 itself by inhibiting one or more enzymes involved in steroidogenesis (17βHSD1, aromatase, sulfatase) (Hong, Y.; Chen, S. *Mol. Cell. Endocrinol.* 2011, 340, 120).

Estrogen sensitive types of breast cancer, female genital tract cancer and lung cancer (non-small cell lung cancer—NSCLC) are characterized by an increased expression of 17βHSD1. Increased E2 levels are then associated with a number of benign anomalies. The most common of these include endometriosis (pathological localization of the uterine lining elsewhere than in the uterine cavity), adenomyosis (moving the uterine cavity lining—the endometrium—into the uterine muscle layer), menorrhagia (abnormally strong menstrual bleeding), metrorrhagia (acyclical, dysfunctional bleeding), dysmenorrhea (pain and other difficulties associated with menstruation) and uterine myomas (WO 2008034796 A2).

17βHSD5 is expressed mainly in the testes, it is commonly found also in the prostate, liver and adrenal glands. Some types of breast and prostate tumors have increased expression (Dufort et al. *Endocrinology.* 1999, 140, 568). Among other isoenzymes, 17βHSD5 has a somewhat special position. As the only one in the 17βHSD family of enzymes, it belongs to so-called aldo-ketoreductases, while the other types are dehydrogenases/short chain reductases. In addition, thanks to a very spacious binding site, it exhibits a certain substrate multispecificity. That is, although it preferentially reduces 4-androsten-3,17-dione to T, it also binds some other estrogens and androgens and affects their conversion at the 3α-, 17β- and 20α-positions. 17βHSD5 is also involved in the synthesis of prostaglandins (prostaglandin $PGF_{2\alpha}$). $PGF_{2\alpha}$ has been shown to play an important role in the growth of some types of tumors, particularly colorectal carcinoma (Qualtrough, D. *Int. J. Cancer* 2007, 121, 734). Since the effect of 17βHSD5 has been demonstrated on the progression of both steroid-sensitive and non-sensitive carcinomas, selective inhibition of 17βHSD5 has long been one of the challenges for further research.

The most common cancer in women is breast cancer. The standard procedure for the treatment of early stages of estrogen-positive breast cancer types is surgery and subsequent adjuvant chemotherapy. In the context of subsequent therapy, selective estrogen receptor modulators (SERMs) such as Tamoxifen, Raloxifen and others are most often used in premenopausal women. These are partial or complete ER antagonists. In postmenopausal women whose tumors have ER+ status, Tamoxifen remains the drug of choice. In the case of ER− breast tumors, SEEMs (Selective Estrogen Enzyme Modulators) are a good choice, such as Tibolon or Anastrozole. These substances selectively affect the respective enzymes of steroidogenesis, aromatase, sulfatase and sulfotransferase. The disadvantage of long-term SERM and SEEM treatment is a frequent occurrence of serious side effects. In the case of SERM, it is vaginal bleeding, endometrial carcinoma, the need for hysterectomy, ischemic cerebrovascular events and venous thromboembolism (Demissie et al. J. Clin. Oncol. 2001, 19, 322). After SEEM application, increased bone breakage, constipation/diarrhea, nausea and vomiting, sleep disturbances, fatigue/weakness, flushing and sweating, vaginal haemorrhage, hair loss, weight changes, depression and others are observed (Eastell et al. J. Clin. Oncol. 2008, 26, 1051). A substantial portion of breast tissue tumors show increased expression of 17βHSD1. It is believed that with modulation of 17βHSD1 activity it would be possible to influence the local E2 level in the affected tissue and thereby regulate the growth of tumor tissue. None of the 17βHSD1 inhibitor has undergone clinical trials yet.

Treatment of prostate cancer is based on a decrease in androgen levels. This can be achieved by surgical or pharmacological (hormonal) castration, or by their appropriate combination. Hormonal therapy consists either of stopping the production of testosterone in testes (LHRH analogues of gonadotrophins), or of blocking the androgen receptor in the prostate cell with antiandrogens (eg. cyproterone acetate). With antiandrogen therapy, side effects are significant, too, including impotence, hot flushes, gynecomastia, mastodynia, digestive problems, depression, fatigue, malaise, and more. A substantial portion of prostate tumors also show increased expression of 17βHSD5. It is believed that with modulation of activity it would be possible to influence the local T level in the affected tissue and thereby regulate the growth of tumor tissue.

A number of 17βHSD inhibitors are described in the literature. Particular emphasis is placed on the preparation of selective, reversible 17βHSD1 inhibitors with minimal or no estrogenic effect. Although research in this area is very intense and involves countless in vitro and in vivo studies, no selective 17βHSD1 inhibitor has so far been in the clinical phase of testing as a potential therapeutic agent for the treatment of estrogen-dependent types of diseases (Poirier, D. Expert Opin. Ther. Patents 2010, 20, 1123).

The 17βHSD1 and 17βHSD5 inhibitors can be structurally divided into two large groups, namely non-steroidal inhibitors and steroid-based inhibitors. Since the present invention discloses inhibitors that are estrone derivatives, only the group of steroid inhibitors of 17βHSD1 and 17βHSD5 will be further discussed. The topic of 17βHSD inhibitors was covered in several reviews (Penning, T. M.; Ricigliano, J. W. J. Enzyme. Inhib. 1991, 5, 165; Poirier, D. Curr. Med. Chem. 2003, 10, 453; Brožič et al. Curr. Med. Chem. 2008, 15, 137; Poirier, D. Anti-cancer Agents Med. Chem. 2009, 9, 642; Day et al. Minerva Endocrinol. 2010, 35, 87).

The following overview will focus on the development in the field of inhibitors of 17βHSD1, especially from 1990 until present. Inhibitory activity against 17βHSD1 has been tested for progestin derivatives, e.g., nomegestrol acetate, medrogestone, tibolone and their metabolites, using the cancerous lines MCF-7 and T-47D (estrogen-dependent breast cancers) at the physiological level of E1. The inhibitors were not selective for 17βHSD1 (e.g., Chetrite et al. J. Steroid Biochem. Molec. Biol. 1996, 58, 525; Chetrite, G. S.; Pasqualini, J. R. J. Steroid Biochem. Molec. Biol. 2001, 76, 95; Shields-Botella et al. J. Steroid Biochem. Mol. Biol. 2005, 93, 1). The effect of Dydrogesterone (Duphaston®) and its 20-dihydro metabolite on the E1 conversion to E2 was also tested (Chetrite, G. S. et al. Anticancer Res. 2004, 24, 1433).

A series of 17 estratrienes fluorinated at the C-17 position was prepared by Deluca et al. and tested for inhibitory activity against the five isoforms of 17βHSD (1, 2, 4, 5, 7). The compounds showed an average inhibitory activity against 17βHSD1 and a poor selectivity against the other isoforms tested. The study of estrogenic potential of substances was not the subject of this study (Deluca et al. Mol. Cell. Endocrinol. 2006, 248, 218).

A series of variously substituted E2-based compounds with inhibitory activity against 17βHSD1 (also tested for isoforms 2 and 3) were prepared in the D. Poirier group. The inhibitor carrying butyl(methyl)thiaheptanamide substituent on the C-6 carbon exhibited 40% inhibitory activity at a concentration of $\mu mol\,l^{-1}$ (Poirier et al. J. Steroid Biochem. Mol. Biol. 1998, 64, 83). Subsequently, so-called dual inhibitors, simultaneously carrying two pharmacophores in the C-16 position, were also prepared. The best of the prepared derivatives also exhibited anti-estrogenic effects (Pelletier et al. Steroids 1994, 59, 536; Tremblay, M. R.; Poirier, D. J. Chem. Soc., Perkin Trans. 1 1996, 2765).

Hybrid inhibitors with a steroid skeleton were also prepared, having a side chain of different lengths carrying adenosine on the C-16 carbon. The best compound, EM-1745, is an excellent competitive, reversible inhibitor (Qiu et al. FASEB J. 2002, 16, 1829; Poirier et al. Synt. Commun. 2003, 33, 3183). In 2005, new series of selective hybrid inhibitors of 17βHSD1 were described (also tested for 17βHSD2 isoenzyme). These were E1 (or 2-ethyl-E1) derivatives bearing a —CH$_2$CONHR group at C16 position. The best of the prepared compounds showed the concentration of the substance necessary for 50% inhibition, i.e., IC$_{50}$, in the range of 27-37 $nmol\,l^{-1}$ at a concentration of E1=2 $nmol\,l^{-1}$ (Lawrence et al. J. Med. Chem. 2005, 48, 2759). Simultaneously, inhibitors with C-16α-bromoalkyl and C-16β-bromoalkyl groups have been developed. Although the compounds were potent inhibitors of 17βHSD1, they were estrogenic. Estrogenicity was later eliminated by modification of the steroid skeleton at C-7 position, but this modification led to a decrease in inhibitory activity (Tremblay, M. R.; Poirier, D. J. Steroid Biochem. Mol. Biol. 1998, 66, 179; Blomquist et al. Endocrinol. 1997, 153, 453; Tremblay et al. Steroids 2001, 66, 821). Other modifications of the C-16 side chain of the steroid skeleton have resulted in a large number of enone, enol, phenol, sulfamate and saturated alcohols. However, improvement in inhibitory activity against 17βHSD1 was not achieved (Ciobanu, L. C.; Poirier, D. Chem. Med. Chem. 2006, 1, 1249).

E1/E2 derivatisation at positions C-7, C-16, C-17 was also studied. E1 derivatives were prepared with a pyrazole or isoxazole ring comprising a C—C bond between C-16 and 17 carbons (Sweet et al. *Biochem. Biophys. Res. Comm.* 1991, 180, 1057); series of E1/E2 derivatives, bearing a substituted pyrazole ring, comprising a C—C bond between C-16 and 17 carbons, were also tested. $IC_{50}$ values of derivatives of E1-C16-methylcarboxamides ranged from tens of nmol·l$^{-1}$ (Allan et al. *J. Med. Chem.* 2006, 49, 1325). For the group of N- and C-substituted 1,3,5(10)-estratriene-[17,16-c]-pyrazole derivatives, the inhibitory activity was worse, ranging in hundreds of nmol·l$^{-1}$. The N-substitution of the pyrazole ring, however, suppresses the estrogenicity of these derivatives. The later prepared derivatives had much better $IC_{50}$ values determined on T-47D cells (WO2004085457; Vicker et al. *Chem. Med. Chem.* 2006, 1, 464). In summary, E1/E2 derivatisation at positions C-7, C-16, C-17, and the biological activity of the most promising inhibitors is discussed in (Purohit et al. *Mol. Cell. Endocrinol.* 2006, 248, 199).

E1/E2 derivatization at C-3, C-16, C-17 was also tested. The best of the 17βHSD1 inhibitors tested was 16β-m-carbamoylbenzyl-E2 (E2B), able to reduce proliferation induced by the physiological level of E1 in T-47D ER+ cells by 62%. Cell growth was not stopped by 100% because the substance itself exhibited weak estrogenicity (Laplante et al. *Bioorg. Med. Chem.* 2008, 16, 1849). Therefore, its 16β, 17β-γ-lactone was prepared. The substance was not estrogenic, but its inhibitory activity against 17βHSD1 significantly decreased. The E2B derivative, which carried the bromoethyl chain instead of the 3-OH group, demonstrated that for the successful inhibition of 17βHSD1, the presence of the 3-OH group on the A-ring of the steroid skeleton was not necessary. This substance is not estrogenic, it is a competitive irreversible selective inhibitor, and was tested in vivo on mouse xenograft model with T-47D cells. It was shown that at a dose of 250 μg/day/mouse, the tumor was reduced by 74% after 32 days (WO2012129673, Ayan et al. *Mol. Cancer. Ther.* 2012, 11, 2096; Maltais et al. *J. Med. Chem.* 2014, 57, 204).

Messinger et al. prepared a large series of C-15α/β-E1 derivatives, some of which had a hydroxyl group in the C-3 position, and others had its methyl-ether, and showed excellent inhibitory activity. Selectivity and estrogenicity were not discussed (Messinger et al. *Mol. Cell. Endocrinol.* 2009, 301, 216; WO2005047303, US20050192263). The same authors also patented 17-difluoroestratiens substituted at the C-15 position by a chain bearing in most cases an amide functional group (WO2006125800, US20060281710). Again, this is a large group of substances with high inhibitory activity, usually sufficiently selective for 17βHSD1 (WO2008065100). The authors described a method of measuring estrogenicity, however estrogenicity is not quantified in the document. A series of estratrienes substituted at the C-15 position by triazole derivatives is described in WO2008034796 and US20080146531. It is a very large group of substances with excellent inhibitory activity of about 90% at a concentration of 1 μmol·l$^{-1}$. Selected derivatives are selective inhibitors of 17βHSD1 (also tested for 17βHSD2 and 3 isoenzymes).

Estratrienes substituted at the C-15 position with triazole derivatives, with a steroid skeleton modified at C-2, 3, 4, 15 and 17 positions, are selective inhibitors of 17βHSD1 (WO2014207311, WO2014207309, WO2014207310).

17βHSD1 inhibitors also include C-2-D-homo-E1 derivatives; the most active is 2-phenethyl-D-homo-E1 with $IC_{50}$=15 nmol·l$^{-1}$ (Möller et al. *Bioorg. Med. Chem. Lett.* 2009, 19, 6740; WO2006003012).

The new 2-substituted estra-1,3,5(10)-trien-17-ones are described in U.S. Pat. No. 7,419,972 (WO2006003013). Their inhibitory activity towards 17βHSD1 is characterized by $IC_{50}$ values ranging from tens to hundreds of nmol·l$^{-1}$.

As far as we know to date, C-15 estrone derivatives as 17βHSD1 inhibitors are the subject of only a few of the above-mentioned patents of Solvay Pharmaceuticals (J. Messinger) and Forendo Pharma LTD (L. Hirvela) and one publication (Messinger et al. *Mol. Cell. Endocrinol.* 2009, 301, 216-224).

In all of these cases, they are structurally very similar substances, but they differ considerably from our derivatives. Our presented derivatives exhibit a more advantageous and complex set of biological properties.

17βHSD5 Inhibitors

C-3,17 and 18-oxirane steroid derivatives have been prepared, but their inhibitory activity and selectivity have not yet been published (Penning et al. *Molec. Cell. Endocr.* 2001, 171, 137). Selective inhibition of 17βHSD5 has been described for J2404 derivative (Deluca et al. *Mol. Cell. Endocrinol.* 2006, 248, 218). From the spirolactone series tested, the EM1404 derivative (3-carboxamido-1,3,5-(10)-estratrien-17(R)-spiro-2-(5,5-dimethyl-6-oxo)tetra-hydropyran) was the best competitor and selective inhibitor with $IC_{50}$=3,2 nmol·l$^{-1}$ and $K_i$=6,9 nmol·l$^{-1}$ (Qiu et al *J. Biol. Chem.* 2007, 282, 8368; WO9946279).

A similar spirolactone prepared by Bydal et al., 3-deoxyestradiol with C-17-dimethyl-spiro-δ-lactone showed $IC_{50}$=2.9 nmol·l$^{-1}$. The substance is only negligibly estrogenic and is not androgenic, but selectivity to individual isoenzymes is not discussed (Bydal et al. *Eur. J. Med. Chem.* 2009, 44, 632). A synthesis of two series of C-17-spirolactone derivatives of androstane was also published. Substances do not bind to ER or exhibit androgenic activity, they inhibit 17βHSD5 in the range of 54-73% at a concentration of 0.3 μmol·l$^{-1}$ (Djigoué et al. *Molecules* 2013, 18, 914). Bothe and co-authors have recently introduced a series of estra-1,3,5(10),16-tetraene-3-carboxamide derivatives (WO2013045407, WO2014128108). The compounds carry a variously substituted pyridine ring at the C-17 position and have been introduced as inhibitors of 17βHSD5, $IC_{50}$<50 nmol·l$^{-1}$. The synthesis and use of C-3 substituted estra-1,3,5(10),16-tetraenes with a similar $IC_{50}$ value is presented in WO2014009274.

DISCLOSURE OF THE INVENTION

This patent application presents a group of new C-15 derivatives of estrone, which specifically inhibit 17β-HSD1 and/or 17β-HSD5 isoenzymes, without simultaneously affecting other tested isoenzymes (in particular 17β-HSD type 2, 3, 4, 7) at the given concentration.

The subject of the present invention are 15β-substituted derivatives of estrone of general formula I,

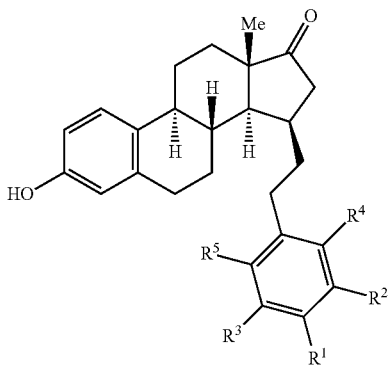

(I)

wherein:
  substituents R¹, R², R³, R⁴, R⁵ are independently selected from the group consisting of: $C_1$-$C_4$ alkyl; $C_1$-$C_4$ alkoxy; $C_1$-$C_4$ halogenalkyl; halogen; and COOR⁶, wherein R⁶ is $C_1$-$C_4$ alkyl, H or OH;
  or R¹ and R² together form an aryl, preferably naphthyl, in which case R³, R⁴ and R⁵ are hydrogen atoms;
and wherein the aromatic ring in position C-15 can be mono-, di-, tri-, tetra- and penta-substituted with the substituents R¹-R⁵.

As used herein, the term "alkyl" refers to a saturated straight or branched $C_1$-$C_4$ alkyl chain, i.e. methyl, ethyl, propyl, isopropyl, butyl, isobutyl or t-butyl.

As used herein, the term "alkoxy" refers to —OR$_a$ group, wherein R$_a$ is alkyl as defined above. Examples include methoxy, ethoxy, propoxy, isopropoxy, butoxy, isobutoxy, t-butoxy and the like. As used herein, the term "aryl" refers to a hydrocarbon group containing from 6 to 10 carbon atoms forming at least one aromatic ring. Preferably, aryl is selected from a group containing phenyl, benzyl, naphthyl; aryl can be unsubstituted or substituted with 1 to 5 substituents selected from —OH, halogen, $C_1$-$C_4$ alkyl, $C_1$-$C_4$ alkoxy, —CN, and —COOR$_b$, where R$_b$ is hydrogen or $C_1$ to $C_4$ alkyl. Halogen is selected from the group consisting of —F, —Cl, —Br, —I.

To the extent of considered therapeutic concentrations, these compounds do not have estrogenic nor toxic effects. Selected derivatives additionally exhibit features of ER/AR antagonists and/or antiproliferative effect in vitro.

The compounds according to the present invention exhibit a unique set of properties, thanks to which they can be useful in therapy and diagnosis of estrogen-dependent diseases. They are selective inhibitors of 17βHSD, they do not have estrogenic activity and they are generally not cytotoxic. By selective inhibition of 17β-hydroxysteoid dehydrogenases (17βHSD), having a key role in the formation of biologically active estrogens and androgens, they may dramatically influence many processes in the body, in particular cell proliferation and differentiation.

Overexpression of studied isozymes from the 17βHSD series, and therefore excessive production of 17β-hydroxysteroids in tissues, is associated with the occurrence of estrogen/androgen-dependent diseases, such as tumors of the breast tissue, ovarian cancer, endometrial cancer, prostate cancer, colorectal cancer, lung cancer, squamous cell carcinoma and also non-tumor disorders like acne, hirsutism, pseudohermaphroditism and many others. Selective inhibition of the various isoenzymes can therefore contribute to the treatment of these diseases. Determining the expression rate of the respective HSD types in the affected tissues then provides a marker for their early diagnosis.

Compounds according to the present invention are preferably prepared by a novel method, which is the cross-metathesis reaction of derivatives of 15β-vinylestrone with appropriate alkenes, catalysed by ruthenium complexes in organic solvents. Subsequent two synthetic steps then use conventional methods to obtain the target molecule.

Structural basis for the present compounds is 3-hydroxy-estra-1,3,5(10)-trien-17-one (estrone), in which the following numbering of carbon atoms is used:

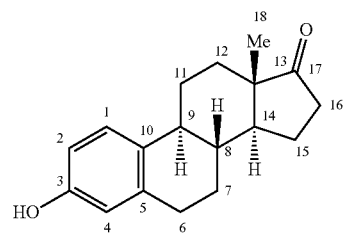

The subject of the present invention is further a method for preparing compounds of general formula I according to the present invention, comprising the following steps:
a) 3-(t-Butyldimethyl silyloxy)-15β-vinyl-estra-1.3.5(10)-trien-17-one reacts in a cross metathesis reaction with a second olefin in the presence of a ruthenium catalyst at temperature from 40° C. to 70° C. under inert atmosphere to form 3-(t-butyldimethylsilyloxy)-15β-vinyl-estra-1.3.5(10)-trien-17-one terminal vinyl-substituted derivatives; preferably, the reaction is performed in a solvent selected from a group comprising dichloromethane, trifluorotoluene, octafluorotoluene, hexafluorobenzene and mixtures thereof, most preferably the solvents used are dichloromethane and trifluorotoluene; preferably, CuI is used as a co-catalyst together with the ruthenium catalyst, in which case the amount of CuI is smaller or equal to the quantity of the ruthenium catalyst;
b) the product of the cross metathesis reaction from the previous step is deprotected (t-butyldimethylsilyl protecting group is removed), preferably using tetrabutylammonium fluoride (TBAF) as a deprotecting agent;
c) hydrogenation of the unsaturated deprotected product of the step b) leading to formation of the compound of general formula (I).

Respective second olefins in step a) are selected from derivatives of styrene, vinylnaphtalene, vinylphenol, vinylbenzene, either of which can be further substituted with halogen, alkyl (as defined above), haloalkyl, alkoxy (as defined above) and/or acetoxy group; more preferably second olefins in step a) are selected from a group containing styrene, 4-(trifluoromethyl)styrene, 4-fluorostyrene, 4-chlorostyrene, 4-vinyl-methylbenzoate, 2-vinylnaphtalene, 4-methoxystyrene, 3-methoxystyrene, 3,4-dimethoxystyrene, 4-ethoxystyrene, 4-t-butoxystyrene, 4-acetoxystyrene, 4-vinylphenol, 4-methylstyrene, 3,4,5-trifluorostyrene, 2,3,4,5,6-pentafluorstyrene.

The ruthenium catalyst is selected from a group comprising Hoveyda Grubbs catalyst second generation, Hoveyda Grubbs catalyst first generation, Grubbs catalyst second generation, Grubbs catalyst first generation.

Removal of t-butyldimethylsilyloxy protecting group in step b) can be performed by conventional deprotection reactions, known to the person skilled in the art. Particularly, deprotection using TBAF is suitable.

Hydrogenation in step c) is preferably performed using Pd/C catalyst and $H_2$ (g).

In a preferred embodiment, the method for preparing compounds of general formula I according to the present invention contains the following steps:

in the first step, to a solution of 3-(t-butyldimethylsilyloxy)-15β-vinyl-estra-1.3.5(10)-trien-17-one and the respective second olefin in a solvent mixture of $CH_2Cl_2$/trifluorotoluene in a volume ratio of 2/1 under an inert atmosphere are added Hoveyda-Grubbs ruthenium catalyst second generation and CuI respectively; preferably, 1 equiv. of 3-(t-butyldimethylsilyloxy)-15-0-vinyl-estra-1.3.5(10)-trien-17-one, 2 equiv. of the respective olefin and 0.1 equiv. of the Hoveyda-Grubbs ruthenium catalyst second generation and CuI are used;

the resulting mixture is first stirred at 40-70° C. for 4-12 hr, and after further addition of the respective second olefin (preferably 2 equiv.) and the Hoveyda-Grubbs ruthenium catalyst (preferably 0.05 equiv.) at the same temperature overnight;

then the reaction is quenched by evaporation of solvents (preferably under reduced pressure) and products of cross-metathesis are obtained by chromatography on silica gel;

in the second step, solution of TBAF in tetrahydrofuran (THF) is successively dropwise added to the metathesis product, dissolved in THF, at room temperature; after 1 h, water is added and the reaction mixture is extracted with $CH_2Cl_2$ and/or $CHCl_3$; the combined organic phases are then washed with saturated NaCl solution, dried with $MgSO_4$; the solvents are removed under reduced pressure and deprotected products are isolated by chromatography on silica gel; and in a third step, the flask with a mixture of deprotected product of metathesis in ethyl acetate (EtOAc) and Pd/C catalyst (10% wt.) is evacuated under vigorous stirring, and then filled with hydrogen; the reaction mixture is stirred overnight, then filtered through Celite (diatomaceous earth $SiO_2$), and after removal of solvent under reduced pressure; final crystalline product can be obtained e.g. by high performance liquid chromatography.

The subject of the present invention are further compounds of general formula I for use as a medical drug.

The subject of the present invention are also compounds of general formula I for use in the diagnosis and/or treatment of estrogen-dependent diseases.

The subject of the present invention is further a pharmaceutical composition comprising at least one of the compounds of general formula I as the active ingredient and a pharmaceutically acceptable carrier. The pharmaceutically acceptable carrier is preferably selected from a group comprising fillers, such as sugars, for example lactose, sucrose, mannitol or sorbitol; binders, such as starches, for example maize, wheat, rice or potato starch; and/or desintegrators, such as carboxymethyl-starch, cross-linked polyvinylpyrrolidone. Additional excipients might be flow regulators and lubricants, for example salicylic acid, talc, stearic acid or salts thereof, such as magnesium stearate or calcium stearate, and/or polyethylene glycol, or derivatives thereof.

Another subject of the present invention is the pharmaceutical composition, comprising at least one of the compounds of general formula I, for use in the diagnosis and/or treatment of estrogen-dependent diseases and disorders.

The estrogen-dependent diseases are preferably selected from breast cancer, ovarian cancer, uterine cancer, endometriosis, adenomyosis, menorrhagia, metrorrhagia, dysmenorrhea, uterine fibroids, polycystic ovarian syndrome, fibrocystic disease of the breast, prostate cancer, non-small cell lung cancer (NSCLC), squamous cell carcinoma, colorectal carcinoma, gastric cancer, acne, hirsutism, pseudohermaphroditism, seborrheic dermatitis, androgens induced alopecia, hyperestrogenism. The pharmaceutical composition, comprising at least one of the compounds of general formula I, can be also used in the treatment of infertility, to induce premature menopause, for hormonal castration, or for use as a contraceptive.

Another subject of the present invention are compounds of general formula I and/or the method for preparing compounds of general formula I according to the present invention, for use in diagnosis and/or treatment of estrogen-dependent diseases, selected from breast cancer, ovarian cancer, uterine cancer, endometriosis, adenomyosis, menorrhagia, metrorrhagia, dysmenorrhea, uterine fibroids, polycystic ovarian syndrome, fibrocystic disease of the breast, prostate cancer, non-small cell lung cancer (NSCLC), squamous cell carcinoma, colorectal carcinoma, gastric cancer, acne, hirsutism, pseudohermaphroditism, seborrheic dermatitis, androgens induced alopecia, hyperestrogenism; and/or for the treatment of infertility, to induce premature menopause, for hormonal castration, or for use as a contraceptive.

Figure 2A:
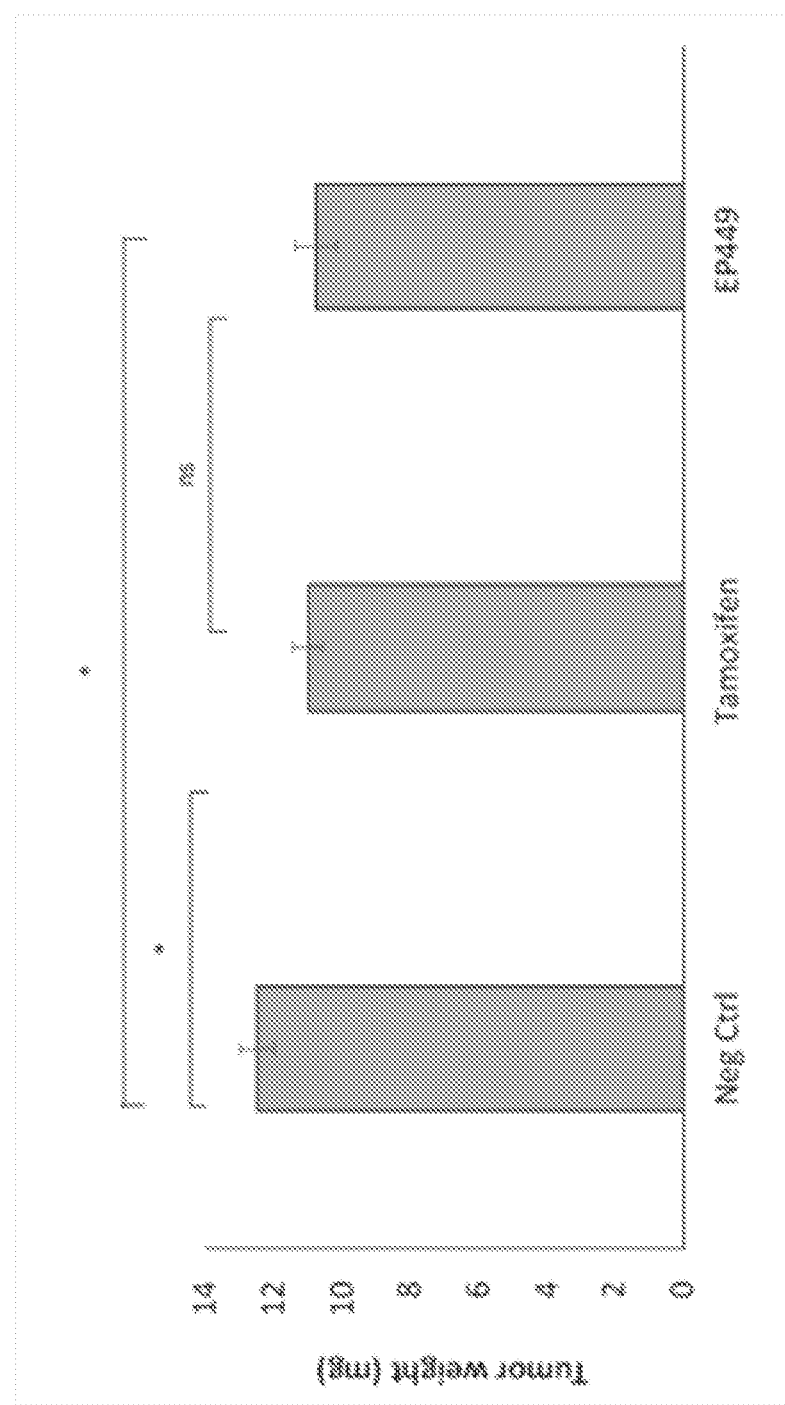
FIGS. 2 A, B C present an efficacy of compound 9 on breast carcinoma tumors initiated from T47D cell lines.

The FIG. 2A presents the mean tumor weight (mg) measured in the different experimental groups after 6 days of treatment on chorioallantoic membrane (CAM).

Figure 2B:
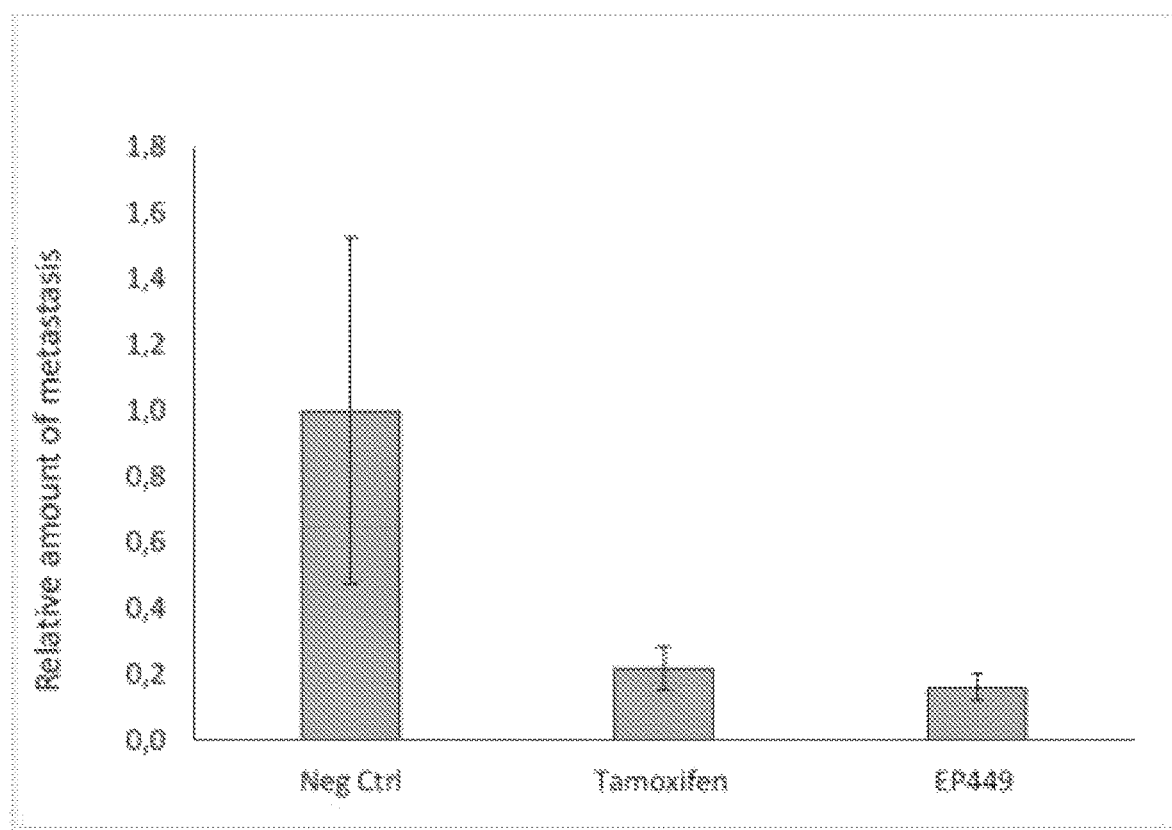

The FIG. 2B presents data analysis of metastasis invasion, measured by qPCR for Alu sequences in lower CAM.

Figure 2C:
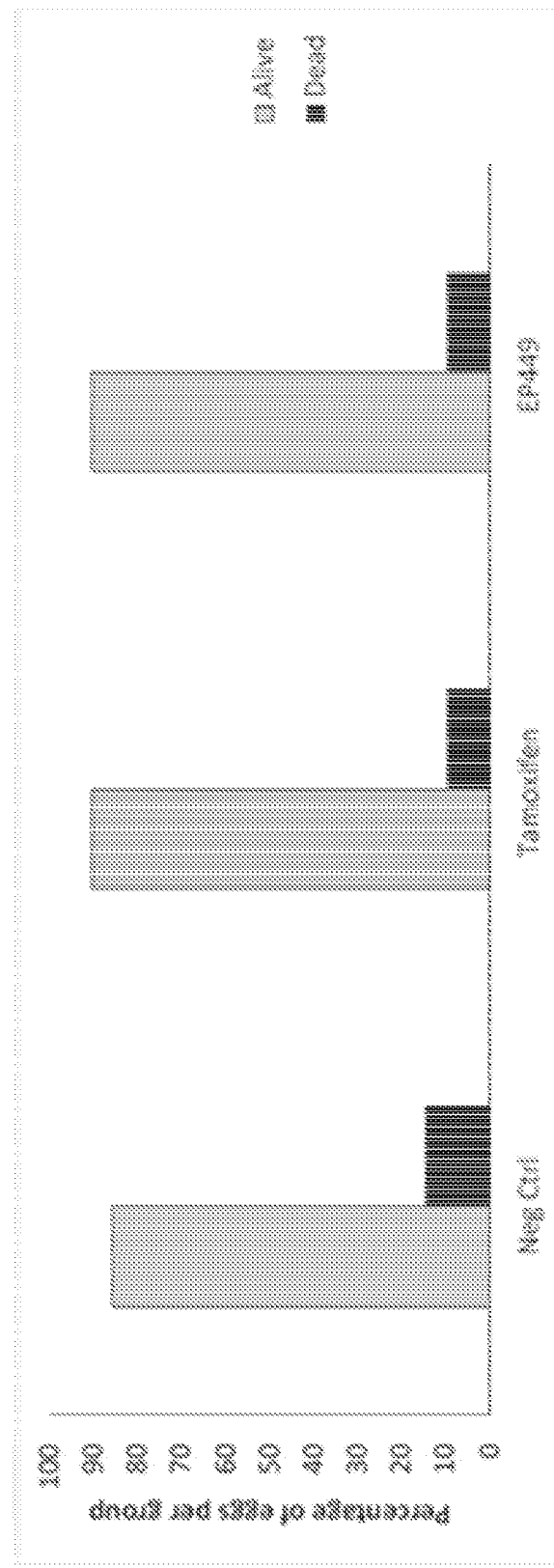

The FIG. 2C presents the number of dead and surviving embryo after 6 days of treatment in the different experimental groups.

For FIGS. 2A and 2B, statistically difference between groups are visible on graphs by presence of stars with the following signification: —No stars: statistically no different (p value>0.05); one star (*): 0.05≥p value>0.01

EXAMPLES

List of Abbreviations $[\alpha]_D$ specific rotation
δ chemical shift
σ standard deviation
A549 human lung adenocarcinoma
Ac acetyl
AKR aldo-keto reductases
APCI atmospheric pressure chemical ionization
AR androgen receptor
b broad signal in NMR spectrum
BJ human fibroblasts
Bu butyl
cDNA complementary DNA
CEM T-lymphoblastic leukemia CEM-DNR-bulk T-lymphoblastic leukemia resistant to doxorubicin
CHO cancer of hamster ovarian
d dublet
DHEA dehydroepiandrosteron
DMEM Dulbecco's Modified Eagle's Medium
DMSO dimethyl sulfoxide
DNA deoxyribonucleic acid
E1 estrone
E2 estradiol
E3 estriol
eq equivalent
ER estrogen receptors
ERE estrogen response elements (DNA sequences capable of binding estrogen receptors)
ESI electrospray ionization
EST estrogen sulfotransferase
Et ethyl
FBS fetal bovine serum
HCT116p53 wt human colon cancer, wild-type
HCT116p53−/− human colon cancer, mutant p53
HMPA hexamethylphosphoramide
HPLC high performance liquid chromatography
HR-MS high resolution mass spectrometry
HSD hydroxysteroid dehydrogenases
$IC_{50}$ the concentration of compound required for 50% inhibition
IR infrared spectroscopy
J coupling constant
K562 human myeloid leukemia
K562-Tax human myeloid leukemia resistant to taxol
LHRH luteinizing hormonereleasing hormone
m multiplet
MCF-7 cell line derived from a human breast carcinoma
Me methyl
mp melting point
MRC7 human fibroblasts
MTT test colorimetric determination of cell viability
NAD(P) nicotinamide adenine dinucleotide (phosphate)
NMR nuclear magnetic resonance
NSCLC non-small cell lung cancer
P450 cytochrome P450
p53 tumor suppressor gene
$PGF_{2\alpha}$ prostaglandine F2α
pGL4 luciferase reporter vector
PgP multidrug resistance protein
PgR progesterone receptor
ppm parts per million
q quadruplet
$R_f$ retarding factor
s singlet
SDR short-chain dehydrogenases/reductases
SEEM selective modulator of steroidogenesis enzymes
SERD selective estrogen receptors deregulator
SERM selective estrogen receptors modulator
SHBG sex hormone binding globulin
SPE solid phase extraction
STS sulfatase
T testosterone
t triplet
T-47D cell line derived from a human breast carcinoma
TBAF tetrabutylammonium fluoride
TBS t-butyldimethylsilyl
TES triethylsilyl
THF tetrahydrofuran
TLC thin layer chromatography
TMS trimethylsilyl $T_R$ retention time
U2OS human osteosarcoma cells
UV ultra violet rays
wt wild type
wt. % weight percent
$\Delta^5$-diol androstendiol (androst-5-en-3(3β,17β-diol)
Synthetic Procedures $^1$H NMR spectra were measured at 400.1 and 500.1 MHz at 24° C. on Bruker AVANCE-400 and 500 spectrometers. $^{13}$C NMR spectra were measured at 100.8 MHz. For standardization of $^1$H NMR spectra the internal signal of tetramethylsilane (δ 0.0, $CDCl_3$) or residual signals of deuterochloroform (δ 7.26) or residual signals of deuteromethanol (δ 3.31) were used. In the case of $^{13}$C spectra the residual signal of deuterochloroform (δ 77.00) or residual signals of deuteromethanol (δ 49.00) were used. The chemical shifts are given in ppm (δ scale); the coupling constants J are given in Hz. Signal multiplicities are designated as follows: s singlet, d doublet, t triplet, q quadruplet, m multiplet, b denotes a broad signal. Melting points were measured on a Kofler bench. Optical rotations were measured on Autopol IV polarimeter (Rudolph Research Analytical, Flanders, USA), $[\alpha]_D$ values are given in $10^{-1}\cdot deg\cdot cm^2\cdot g^{-1}$ and were compensated to a standard temperature of 20° C. Infrared spectra were measured in sample solutions or in KBr tablets using a Bruker IFS 55 spectrometer; frequency is given in $cm^{-1}$. Mass spectra were measured on a ZAB-EQ spectrometer (at 70 eV) or LCQ Classic (Thermo Finnigan). HPLC chromatography was performed on a Waters 600 device with diode array detector PDA 2996. Fluka 60 silica gel was used for column chromatography, aluminium plates coated with a layer of silica gel 60 $FB_{254B}$ were used for thin layer chromatography (TLC). $KMnO_4$ and phosphomolybdic acid solutions and UV detection were used to visualize TLC.

Synthesis of the Starting Compound

Example 1: 3-(t-Butyldimethylsilyloxy)-estra-1,3,5(10),15-tetraen-17-one (1)

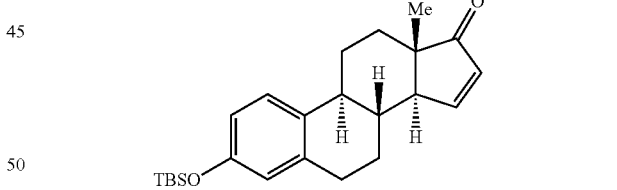

Enone 1 was prepared according to a published method (Sakakibara, M.; Uchida, A. O. *Biosci. Biotech. Biochchem* 1996, 60, 3, 405) by Saegusa oxidation in 75% yield: mp 148° C.; $[\alpha]_D$ −37.4 (c 0.203; $CHCl_3$); $^1$H NMR (500 MHz, $CDCl_3$) δ 0.19 (s, 6H, Si—$(CH_3)_2$), 0.98 (s, 9H, $(CH_3)_3$—C), 1.11 (s, 3H, H-18), 1.55 (m, 1H, H-7a), 1.66-1.85 (m, 3H, H-8, 11a, 12a), 2.01 (m, 1H, H-12b), 2.18 (dm, 1H, J=12.9 Hz, H-7b), 2.33 (m, 1H, H-9), 2.43 (m, 1H, H-11a), 2.50 (dm, 1H, J=11.6 Hz, H-14), 2.87-2.96 (m, 2H, H-6), 6.08 (dd, 1H, J=6.0; 3.2 Hz, H-16), 6.59 (bd, 1H, J=2.7 Hz, H-4), 6.64 (dd, 1H, J=8.5; 2.7 Hz, H-2), 7.12 (d, 1H, J=8.5 Hz, H-8), 7.63 (dd, 1H, J=6.0; 1.9 Hz, H-15); $^{13}$C NMR (150.9 MHz, $CDCl_3$) δ −4.41 (Si—$(CH_3)_2$), 181.5 (C—$(CH_3)_3$), 20.97 (C-18), 25.34 (C-11), 25.67 (C—$(CH_3)_3$), 26.68 (C-7), 29.08 and 29.19 (C-6, 12), 35.48 (C-8), 45.15

(C-9), 51.46 (C-13), 56.13 (C-14), 117.33 (C-3), 120.01 (C-4), 125.82 (C-1), 131.87 (C-16), 132.28 (C-10), 137.31 (C-5), 153.58 (C-3), 158.26 (C-15), 213.09 (C-17); IR (CHCl$_3$) v 3076, 3050, 3029, 2960, 2932, 2897, 2860, 1705, 1615, 1607, 1569, 1497, 1472, 1463, 1443, 1436, 1417, 1391, 1371, 1363, 1258, 1186, 1104, 1005, 941, 885, 697, 582, 449 cm$^{-1}$; HR-MS (ESI) calculated for C$_{24}$H$_{34}$O$_2$SiNa [M+Na$^+$] 405.22203 found 405.22212. R$_f$ (7/1 hexane/EtOAc)=0.6.

Example 2: 3-(t-Butyldimethylsilyloxy)-15β-vinyl-estra-1,3,5(10)-trien-17-one (2)

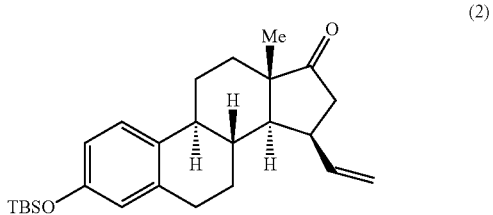

(2)

To our knowledge, the preparation of 15β-vinylestrone was published only in WO200834796. We altered this method so that instead of the benzyl protecting group (giving a reaction yield of 24%) a t-butyldimethylsilyl group was now used. We succeeded to significantly increase yields of vinylestrone 2, which (after crystallization from EtOAc) are reproducibly above 90%.

Mixture of 1 mol·l$^{-1}$ solution of vinylmagnesium bromide in THF (13 ml, 13.08 mmol), CuI (65 mg, 0.654 mmol) and HMPA (2.8 ml, 15.7 mmol) in CH$_2$Cl$_2$ (50 ml) under argon atmosphere was cooled to −78° C. A solution of enone 1 (2.5 g, 6.54 mmol) and TMSCl (1.7 ml, 13.08 mmol) in CH$_2$Cl$_2$ (50 ml) was added dropwise to this mixture. The reaction mixture was then slowly warmed to room temperature and stirred overnight. After adding water and dropwise addition of 1 mol·l$^{-1}$ HCl, the mixture was stirred for 5 minutes, then diluted with CH$_2$Cl$_2$ and washed with water. The combined organic phases were washed with saturated NaCl solution, dried over MgSO$_4$ and concentrated under reduced pressure. After chromatography on silica gel (1/1 hexane/CH$_2$Cl$_2$) 2.5 g vinylestrone 2 was obtained in 92% yield as a white crystalline solid: mp 141° C.; [α]$_D$+52.7 (c 0.186; CHCl$_3$); $^1$H NMR (500 MHz, CDCl$_3$) δ 0.19 (s, 6H, Si—(CH$_3$)$_2$), 0.98 (s, 9H, (CH$_3$)$_3$—C), 1.03 (s, 3H, H-18), 1.41-1.56 (m, 3H, H-7a, 11a, 12a), 1.72-1.83 (m, 2H, H-8, 14), 1.90 (m, 1H, H-12b), 2.15 (m, 1H, H-7b), 2.28 (m, 1H, H-9), 2.36 (m, 1H, H-11a), 2.52 (dd, 1H, J=19.5; 9.0 Hz, H-16b), 2.63 (dd, 1H, J=19.5; 2.2 Hz, H-16a), 2.80-2.92 (m, 2H, H-6), 3.13 (m, 1H, H-15), 5.13 (dt, 1H, J=10.4; 1.6 Hz, H-2b'), 5.17 (dt, 1H, J=17.2; 1.6 Hz, H-2a'), 6.10 (ddd, 1H, J=17.2; 10.4; 6.7 Hz, H-1'), 6.58 (dm, 1H, J=2.7 Hz, H-4), 6.62 (dd, 1H, J=8.4; 2.7 Hz, H-2), 7.11 (dd, 1H, J=8.6; 0.9 Hz, H-1); $^{13}$C NMR (150.9 MHz, CDCl$_3$) δ −4.40 (Si—(CH$_3$)$_2$), 16.87 (C-18), 18.17 (C—(CH$_3$)$_3$), 25.48 (C-11), 25.70 (C—(CH$_3$)$_3$), 26.31 (C-7), 29.24 (C-6), 33.38 (C-12), 35.94 (C-8), 37.10 (C-15), 41.75 (C-16), 44.50 (C-9), 47.69 (C-13), 52.69 (C-14), 115.96 (C-2'), 117.24 (C-2), 119.98 (C-4), 125.85 (C-1), 132.63 (C-10), 137.62 (C-5), 139.00 (C-1'), 153.54 (C-3), 220.40 (C-17); IR (CHCl$_3$) v 3080, 2960, 2932, 2895, 2860, 1732, 1637, 1607, 1570, 1497, 1472, 1463, 1442, 1435, 1419, 1404, 1391, 1377, 1362, 1256, 1186, 1159, 1100, 1008, 1000, 941, 922, 883, 841, 806, 697, 586, 447 cm$^{-1}$; HR-MS (ESI) calculated for C$_{26}$H$_{38}$O$_2$SiNa [M+Na$^+$] 433.25333 found 433.25330. R$_f$ (7/1 hexane/EtOAc)=0.5.

a) General Procedure for Metathesis of Vinylestrone 2 with Various Olefins

To the solution of vinylestrone 2 (100 mg, 0.244 mmol) and second olefin (0.488 mmol) in the mixture of CH$_2$Cl$_2$/trifluorotoluene (21 ml, 2/1), Hoveyda Grubbs second generation catalyst (15 mg, 0.024 mmol) (Sigma Aldrich, catalog number 569755) and CuI (5 mg, 0.024 mmol) were added under argon atmosphere and the resulting mixture was stirred at 40-70° C., preferably 65° C. for 4-12 h, preferably for 4 h. After further addition of second olefin (0.488 mmol) and catalyst (7.5 mg, 0.012 mmol), the mixture was further stirred at the same temperature overnight. Then the solvents were removed under reduced pressure and chromatography of the residue on silica gel (hexane/EtOAc 95/5) yielded the cross metathesis product. Yields of vinylestrone 2 metathesis with various olefins were in the range of 56-98% for majority of the prepared compounds.

b) General Procedure for C-3 TBS Group Deprotection

A solution of TBAF, 1 mol·l$^{-1}$ in THF (1 eq) was added dropwise to the solution of metathesis product in THF at room temperature. After 1 h, water was added and the reaction mixture was extracted with CH$_2$Cl$_2$ and/or CHCl$_3$. The combined organic phases were washed with saturated NaCl solution, dried over MgSO$_4$ and the solvents were removed under reduced pressure. Chromatography on silica gel yielded the deprotected product. The yields of deprotection reactions always exceeded 90%.

c) General Procedure for Reduction of the Double Bond

Flask with a mixture of deprotected metathesis product and Pd/C (10 wt. %) catalyst in EtOAc was evacuated under vigorous stirring and then filled with hydrogen. The reaction mixture was stirred overnight. The progress of the reaction was monitored by TLC using KMnO$_4$ solution for selective visualization of the starting material since R$_f$ values of starting material and product were always the same. Additionally, starting material was usually visible under UV light (254 nm), while the reduced product was not visible at the same wavelength. The reaction mixture was then filtered through Celite, solvents were removed under reduced pressure and chromatography on HPLC (MeCN/H$_2$O) resulted in final colorless crystalline products. The yields were always higher than 90%.

Example 3: 15β-Phenethyl-3-hydroxy-estra-1,3,5(10)-trien-17-one (3)

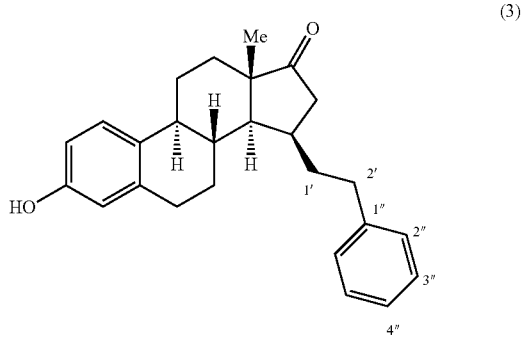

(3)

Compound 3 was prepared according to the above general procedure by reacting vinylestrone 2 with styrene (56 μl). Chromatography on HPLC (30/70 MeCN/H$_2$O, t$_R$=15 min) yielded 36 mg of colorless solid 3 (numbering of the C-15 side chain in all the following examples is the same as in derivative 3): mp 153° C.; [α]$_D$+52.6 (c 0.547; CHCl$_3$); $^1$H NMR (500 MHz, CDCl$_3$) δ 1.03 (s, 3H, H-18), 1.35-1.55 (m, 3H, H-7a, 11a, 12a), 1.62-1.76 (m, 3H, H-8, 14, 1'a), 1.86-1.97 (m, 3H, H-7a, 12b, 1'b), 2.25 (m, 1H, H-9), 2.30-2.38 (m, 2H, H-11b, 15), 2.40 (dd, 1H, J=19.3; 2.8 Hz, H-16a), 2.49 (dd, 1H, J=19.3; 8.1 Hz, H-16b), 2.54 (ddd, 1H, J=13.6; 9.2; 7.1 Hz, H-2'a), 2.75 (ddd, 1H, J=13.6; 9.8; 5.2 Hz, H-2'b), 2.80-2.93 (m, 2H, H-6), 4.82 (bs, 1H, OH), 6.59 (dm, 1H, J=2.8 Hz, H-4), 6.63 (ddm, 1H, J=8.4; 2.8 Hz, H-2), 7.13 (dd, 1H, J=8.5; 1.1 Hz, H-1), 7.18 (m, 2H, H-2"), 7.21 (m, 1H, H-4"), 7.30 (m, 2H, H-3"); $^{13}$C NMR (150.9 MHz, CDCl$_3$) δ 17.71 (C-18), 25.47 (C-11), 26.57 (C-7), 29.30 (C-6), 33.09 (C-1'), 33.73 (C-15), 33.82 (C-12), 35.80 (C-2'), 35.91 (C-8), 42.70 (C-16), 44.47 (C-9), 47.19 (C-13), 52.77 (C-14), 112.70 (C-2), 115.22 (C-4), 126.04 (C-4"), 126.16 (C-1), 128.41 (C-2"), 128.46 (C-3"), 132.33 (C-10), 138.00 (C-5), 141.65 (C-1"), 153.54 (C-3), 221.37 (C-17); IR (CHCl$_3$) ν 3599, 3413, 3086, 3064, 3027, 2929, 2861, 1729, 1603, 1585, 1499, 1454, 1465, 1378, 1261, 1178, 1166, 1151, 1124, 1030, 903, 701, 472 cm$^{-1}$; HR-MS (APCI) calculated for C$_{26}$H$_{30}$O$_2$Na [M+Na$^+$] 397.21380 found 397.21384. R$_f$ (4/1 hexane/EtOAc)=0.4.

Example 4: 15β-(4-(Trifluoromethyl)phenethyl)-3-hydroxy-estra-1,3,5(10)-trien-17-one (4)

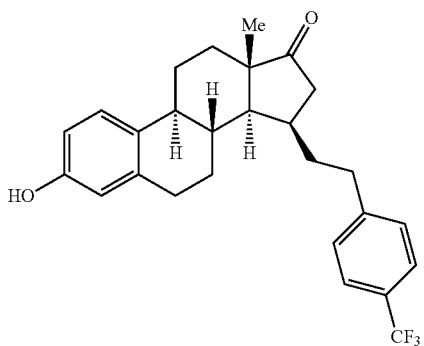

(4)

Compound 4 was prepared according to the above general procedure by reacting vinylestrone 2 with 4-(trifluoromethyl)styrene (72 μl). Chromatography on HPLC (30/70 MeCN/H$_2$O, t$_R$=19 min) yielded 24 mg of colorless solid 4: mp 168° C.; [α]$_D$+51.5 (c 0.136; CHCl$_3$); $^1$H NMR (500 MHz, CDCl$_3$) δ 1.03 (s, 3H, H-18), 1.37-1.55 (m, 3H, H-7a, 11a, 12a), 1.60-1.76 (m, 3H, H-8, 14, 1'a), 1.83-1.97 (m, 3H, H-7a, 12b, 1'b), 2.26 (m, 1H, H-9), 2.30-2.38 (m, 2H, H-11b, 15), 2.41 (dd, 1H, J=19.4, 2.5 Hz, H-16a), 2.47 (dd, 1H, J=19.4; 8.5 Hz, H-16b), 2.60 (bddd, 1H, J=13.8; 9.0; 7.3 Hz, 2'a), 2.81 (bddd, 1H, J=13.7; 9.8; 5.3 Hz, 2'b), 2.82-2.92 (m, 2H, H-6), 4.91 (s, 1H, OH), 6.59 (bd, 1H, J=2.8 Hz, H-4), 6.64 (bdd, 1H, J=8.5; 2.8 Hz, H-2), 7.13 (bd, 1H, J=8.5 Hz, H-1), 7.29 (m, 2H, H-2"), 7.56 (m, 1H, H-3"); $^{13}$C NMR (150.9 MHz, CDCl$_3$) δ 17.72 (C-18), 25.43 (C-11), 26.60 (C-7), 29.24 (C-6), 32.82 (C-1'), 33.71 (C-15), 33.80 (C-12), 35.59 (C-2'), 35.87 (C-8), 42.54 (C-16), 44.43 (C-9), 47.18 (C-13), 52.70 (C-14), 112.75 (C-2), 115.21 (C-4), 124.24 (q, J$^{C-F}$=271.7 Hz, CF$_3$), 125.40 (q, J$^{C-F}$=3.8 Hz, C-3"), 126.15 (C-1), 128.46 (q, J$^{C-F}$=32.4 Hz, C-4"), 128.71 (C-2"), 132.21 (C-10), 137.88 (C-5), 145.73 (q, J$^{C-F}$=1.3 Hz, C-1"), 153.61 (C-3), 220.97 (C-17); $^{19}$F NMR (470.3 MHz, CDCl$_3$) δ −58.46; IR (CHCl$_3$) ν 3598, 3433, 3060, 2938, 2864, 1730, 1618, 1560, 1466, 1453, 1418, 1377, 1326, 1249, 1167, 1128, 1108, 1068, 1095, 1057, 1019, 834, 611, 446 cm$^{-1}$; HR-MS (APCI) calculated for C$_{27}$H$_{29}$O$_2$F$_3$Na [M+Na$^+$] 465.20119 found 465.20102. R$_f$ (4/1 hexane/EtOAc)=0.4.

Example 5: 15β-(4-Fluorophenethyl)-3-hydroxy-estra-1,3,5(10)-trien-17-one (5)

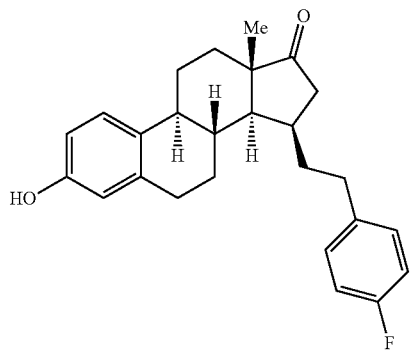

(5)

Compound 5 was prepared according to the above general procedure by reacting vinylestrone 2 with 4-fluorostyrene (58 μl). Chromatography on HPLC (30/70 MeCN/H$_2$O, t$_R$=21 min) yielded 26 mg of colorless solid 5: mp 164° C.; [α]$_D$+33.8 (c 0.222; CHCl$_3$); $^1$H NMR (500 MHz, CDCl$_3$) δ 1.03 (s, 3H, H-18), 1.34-1.56 (m, 3H, H-7a, 11a, 12a), 1.58-1.77 (m, 3H, H-8, 14, 1'a), 1.82-1.96 (m, 3H, H-7a, 12b, 1'b), 2.26 (m, 1H, H-9), 2.28-2.38 (m, 2H, H-11b, 15), 2.39 (bdd, 1H, J=19.4, 2.5 Hz, H-16a), 2.45 (bdd, 1H, J=19.4; 8.5 Hz, H-16b), 2.50 (m, 1H, 2'a), 2.72 (m, 1H, 2'b), 2.78-2.94 (m, 2H, H-6), 5.03 (bs, 1H, OH), 6.60 (bd, 1H, J=2.7 Hz, H-4), 6.64 (bdd, 1H, J=8.4; 2.8 Hz, H-2), 6.99 (m, 1H, H-2"), 7.07-7.20 (m, 3H, H-1, 3"); $^{13}$C NMR (150.9 MHz, CDCl$_3$) δ 17.71 (C-18), 25.44 (C-11), 26.56 (C-7), 29.27 (C-6), 33.16 (C-1'), 33.56 (C-15), 33.79 (C-12), 34.90 (C-2'), 35.88 (C-8), 42.64 (C-16), 44.43 (C-9), 47.20 (C-13), 52.72 (C-14), 112.73 (C-2), 115.20 (d, J$^{C-F}$=21.2 Hz, C-3"), 115.22 (C-4), 126.14 (C-1), 129.72 (d, J$^{C-F}$=7.8 Hz, C-2"), 132.20 (C-10), 137.21 (d, J$^{C-F}$=3.3 Hz, C-1"), 137.92 (C-5), 153.62 (C-3), 161.32 (d, J$^{C-F}$=243.7 Hz, C-4"), 221.3 (C-17); $^{19}$F NMR (470.3 MHz, CDCl$_3$) δ −110.93 (m, 1F); IR (CHCl$_3$) ν 3598, 3431, 3028, 2936, 2864, 1729, 1610, 1585, 1502, 1466, 1453, 1440, 1378, 1281, 1248, 1190, 1157, 1095, 1057, 983, 959, 939, 877, 582, 472 cm$^{-1}$; HR-MS (APCI) calculated for C$_{26}$H$_{29}$O$_2$FNa [M+Na$^+$] 415.20438 found 415.20447. R$_f$(4/1 hexane/EtOAc)=0.4.

Example 6: 15β-(4-Chlorophenethyl)-3-hydroxy-estra-1,3,5(10)-trien-17-one (6)

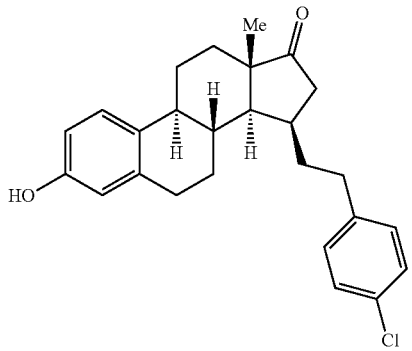

(6)

Compound 6 was prepared according to the above general procedure by reacting vinylestrone 2 with 4-chlorostyrene (59 μl). Chromatography on HPLC (35/65 MeCN/H$_2$O, t$_R$=30 min) yielded 34 mg of colorless solid 6: mp 168° C.; [α]$_D$+69.3 (c 0.150; CHCl$_3$); $^1$H NMR (500 MHz, CDCl$_3$) δ 1.02 (s, 3H, H-18), 1.36-1.56 (m, 3H, H-7a, 11a, 12a), 1.65 (m, 1H, H-1a'), 1.64-1.76 (m, 2H, H-8, 14), 1.84-1.94 (m, 3H, H-1b', 7b, 12b), 2.26 (m, 1H, H-9), 2.26-2.38 (m, 2H, H-11b, 15), 2.40 (dd, 1H, J=19.3, 2.6 Hz, H-16a), 2.44 (dd, 1H, J=19.3; 8.3 Hz, H-16b), 2.50 (ddd, 1H, J=13.8; 8.9; 7.3 Hz, H-1'a), 2.72 (ddd, 1H, J=13.8; 9.5; 5.2 Hz, H-1'b), 2.81-2.93 (m, 2H, H-6), 4.70 (s, 1H, OH), 6.59 (d, 1H, J=2.8 Hz, H-4), 6.63 (dd, 1H, J=8.4; 2.8 Hz, H-2), 7.10 (m, 2H, H-2"), 7.13 (d, 1H, J=8.4 Hz, H-1), 7.21 (m, 2H, H-3"); $^{13}$C NMR (150.9 MHz, CDCl$_3$) δ 17.73 (C-18), 25.45 (C-11), 26.60 (C-7), 29.27 (C-6), 32.96 (C-1'), 33.62 (C-15), 33.82 (C-12), 35.08 (C-2'), 35.89 (C-8), 42.58 (C-16), 44.45 (C-9), 47.17 (C-13), 52.73 (C-14), 112.73 (C-2), 115.21 (C-4), 126.17 (C-1), 128.57 (C-3"), 129.74 (C-2"), 131.79 (C-4"), 132.33 (C-10), 137.95 (C-5), 140.04 (C-1"), 153.54 (C-3), 220.95 (C-17); IR (KBr) ν 3372, 1728, 1711, 1618, 1611, 1501, 1492, 1464, 1407, 1375, 1015 cm$^{-1}$; HR-MS (APCI) calculated for C$_{26}$H$_{30}$O$_2$Cl [M+H$^+$] 409.19288 found 409.19284. R$_f$ (4/1 hexane/EtOAc)=0.4.

Example 7: Methyl 4-(2-(3-hydroxy-estra-1,3,5(10)-trien-17-on-15β-yl)ethyl)benzoate (7)

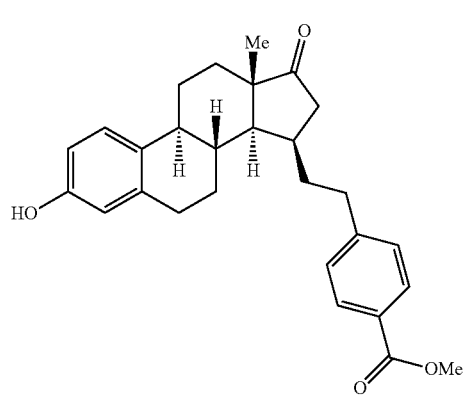

(7)

Compound 7 was prepared according to the above general procedure by reacting vinylestrone 2 with methyl 4-vinylbenzoate (62 μl). Chromatography on HPLC (40/60 MeCN/H$_2$O, t$_R$=30 min) yielded 17 mg of colorless solid 7: mp 139° C.; [α]$_D$+70.2 (c 0.084; CHCl$_3$); $^1$H NMR (500 MHz, CDCl$_3$) δ 1.02 (s, 3H, H-18), 1.34-1.55 (m, 3H, H-7a, 11a, 12a), 1.65-1.76 (m, 3H, H-1'a, 8, 14), 1.82-1.98 (m, 3H, H-1'b, 7b, 12b), 2.25 (m, 1H, H-9), 2.28-2.38 (m, 2H, H-11b, 15), 2.39 (dd, 1H, J=19.3; 2.6 Hz, H-16a), 2.45 (dd, 1H, J=19.3; 8.4 Hz, H-16b), 2.60 (ddd, 1H, J=13.7; 8.8; 7.2 Hz, H-2'a), 2.80 (ddd, 1H, J=13.7; 9.6; 5.3 Hz, H-2'b), 2.80-2.93 (m, 2H, H-6), 3.91 (s, 3H, OCH$_3$), 5.01 (bs, 1H, OH), 6.59 (bd, 1H, J=2.8 Hz, H-4), 6.64 (bdd, 1H, J=8.4; 2.8 Hz, H-2), 7.12 (dd, 1H, J=8.5; 1.0 Hz, H-1), 7.25 (m, 2H, H-2"), 7.98 (m, 2H, H-3"); $^{13}$C NMR (150.9 MHz, CDCl$_3$) δ 17.73 (C-18), 25.43 (C-11), 25.59 (C-7), 29.25 (C-6), 32.68 (C-1'), 33.64 (C-15), 33.80 (C-12), 35.73 (C-2'), 35.87 (C-8), 42.53 (C-16), 44.43 (C-9), 47.17 (C-13), 52.07 (OCH$_3$), 52.71 (C-14), 112.74 (C-2), 115.22 (C-4), 126.13 (C-1), 128.05 (C-4"), 128.48 (C-2"), 129.84 (C-3"), 132.19 (C-10), 137.90 (C-5), 147.14 (C-1"), 153.65 (C-3), 167.09 (CO), 220.99 (C-17); IR (KBr) ν 3406, 3020, 1733, 1720, 1700, 1610, 1584, 1502, 1436, 1415, 1351, 1282, 964 cm$^{-1}$; HR-MS (APCI) calculated for C$_{28}$H$_{33}$O$_4$ [M+H$^+$] 433.23734 found 433.23716. R$_f$ (4/1 hexane/EtOAc)=0.2.

Example 8: 3-Hydroxy-15β-(2-(naphtalen-2-yl)ethyl)-estra-1,3,5(10)-trien-17-one (8)

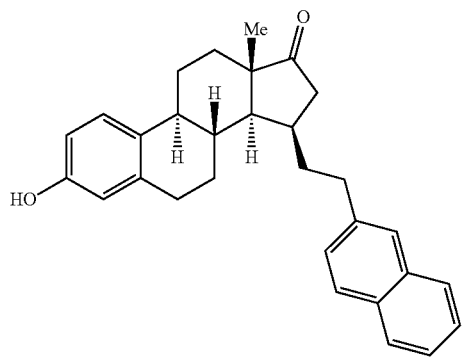

(8)

Compound 8 was prepared according to the above general procedure by reacting vinylestrone 2 with 2-vinylnaphthalene (75 mg). Chromatography on HPLC (30/70 MeCN/H$_2$O, t$_R$=38 min) yielded 13 mg of colorless solid 8: mp 201° C.; [α]$_D$+77.0 (c 0.309; CHCl$_3$); $^1$H NMR (500 MHz, CDCl$_3$) δ 1.05 (s, 3H, H-18), 1.32-1.55 (m, 3H, H-7a, 11a, 12a), 1.66-1.75 (m, 2H, H-8, 14), 1.76 (dddd, 1H, J=13.6; 11.7; 8.9; 5.3 Hz, H-1'a), 1.86-1.95 (m, 2H, H-7b, 12b), 2.02 (dddd, 1H, J=13.6; 9.5; 7.2; 2.1 Hz, H-1'b), 2.24 (m, 1H, H-9), 2.31-2.42 (m, 2H, H-11b, 15), 2.40-2.52 (m, 2H, H-16), 2.71 (ddd, 1H, J=15.8; 8.9; 7.2 Hz, H-2'a), 2.78-2.91 (m, 2H, H-6), 2.92 (ddd, 1H, J=13.8; 9.5; 5.3 Hz, H-2'b), 5.11 (bs, 1H, OH), 6.59 (bd, 1H, J=2.8 Hz, H-4), 6.64 (bdd, 1H, J=8.4; 2.8 Hz, H-2), 7.12 (dd, 1H, J=8.5; 1.1 Hz, H-1), 7.32 (dd, 1H, J=8.4; 1.8 Hz, H-3"), 7.44 (bddd, 1H, J=8.0; 6.8; 1.4 Hz, H-6"), 7.47 (bddd, 1H, J=8.1; 6.8; 1.5 Hz, H-7"), 7.61 (m, 1H, H-1"), 7.79 (m, 1H, H-8"), 7.80 (bd, 1H, J=8.4 Hz, H-4"), 7.82 (m, 1H, H-5); $^{13}$C NMR (150.9 MHz, CDCl$_3$) δ 17.74 (C-18), 25.47 (C-11), 26.62 (C-7), 29.27 (C-6), 32.85 (C-1'), 33.75 (C-15), 32.85 (C-12), 35.89

(C-2'), 35.95 (C-8), 42.71 (C-16), 44.47 (C-9), 47.24 (C-13), 52.82 (C-14), 112.74 (C-2), 115.24 (C-4), 125.30 (C-6"), 126.07 (C-1), 126.11 (C-7"), 126.51 (C-1"), 127.07 (C-3"), 127.35 (C-8"), 127.64 (C-4"), 128.09 (C-5"), 132.06 (C-4a"), 132.28 (C-10), 133.58 (C-8a"), 137.97 (C-5), 139.07 (C-2"), 153.65 (C-3), 221.38 (C-17); IR (KBr) ν 3371, 3052.3018, 1729, 1719, 1610, 1601, 1584, 1502, 1451, 1442 cm$^{-1}$; HR-MS (APCI) calculated for $C_{30}H_{33}O_2$ [M+H$^+$] 425.24751 found 425.24746. $R_f$(4/1 hexane/EtOAc)=0.4.

Example 9: 3-Hydroxy-15β-(4-methoxyphenethyl)-estra-1,3,5 (10)-trien-17-one (9)

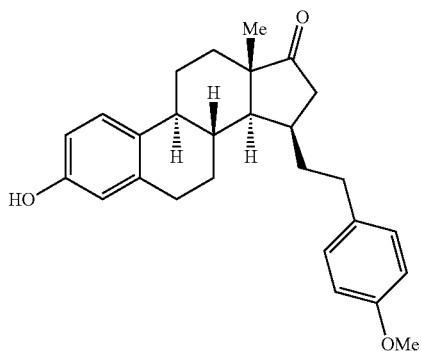

(9)

Compound 9 was prepared according to the above general procedure by reacting vinylestrone 2 with 4-methoxystyrene (65 µl). Chromatography on HPLC (37/63 MeCN/H$_2$O, $t_R$=30 min) yielded 24 mg of colorless solid 9: mp 159° C.; [α]$_D$+48.0 (c 0.154; CHCl$_3$); $^1$H NMR (500 MHz, CDCl$_3$) δ 1.02 (s, 3H, H-18), 1.35-1.55 (m, 3H, H-7a, 11a, 12a), 1.63 (m, 1H, H-1'), 1.65-1.76 (m, 2H, H-8, 14), 1.85-1.94 (m, 3H, H-1'b, 7b, 12b), 2.25 (m, 1H, H-9), 2.28-2.36 (m, 2H, H-11b, 15), 2.39 (dd, 1H, J=19.4; 2.7 Hz, H-16a), 2.44 (dd, 1H, J=19.4; 8.7 Hz, H-16b), 2.49 (ddd, 1H, J=13.8; 9.0; 7.2 Hz, H-2'a), 2.69 (ddd, 1H, J=13.8; 9.7; 5.3 Hz, H-2'b), 2.79-2.93 (m, 2H, H-6), 3.80 (s, 3H, OCH$_3$), 4.69 (bs, 1H, OH), 6.59 (bd, 1H, J=2.8 Hz, H-4), 6.63 (bdd, 1H, J=8.4; 2.8 Hz, H-2), 6.84 (m, 2H, H-3"), 7.09 (m, 2H, H-2"), 7.13 (bd, 1H, J=8.4 Hz, H-1); $^{13}$C NMR (150.9 MHz, CDCl$_3$) δ 17.71 (C-18), 25.49 (C-11), 26.59 (C-7), 29.32 (C-6), 33.27 (C-1'), 33.66 (C-15), 33.83 (C-12), 34.87 (C-2'), 35.93 (C-8), 42.17 (C-16), 44.49 (C-9), 47.19 (C-13), 52.79 (C-14), 55.27 (OCH$_3$), 112.69 (C-2), 113.86 (C-3"), 115.22 (C-4), 126.18 (C-1), 129.30 (C-2"), 132.39 (C-10), 133.69 (C-1"), 130.06 (C-1"), 138.03 (C-5), 153.51 (C-3), 157.89 (C-4"), 221.31 (C-17); IR (KBr) ν 3386, 3059, 2835, 1730, 1718, 1619, 1583, 1512, 1452, 1442, 1246, 1035, 965, 708 cm$^1$; HR-MS (APCI) calculated for $C_{27}H_{33}O_3$ [M+H$^+$] 405.24242 found 405.24235. $R_f$ (4/1 hexane/EtOAc)=0.3.

Example 10: 3-Hydroxy-15β-(3-methoxyphenethyl)-estra-1,3,5(10)-trien-17-one (10)

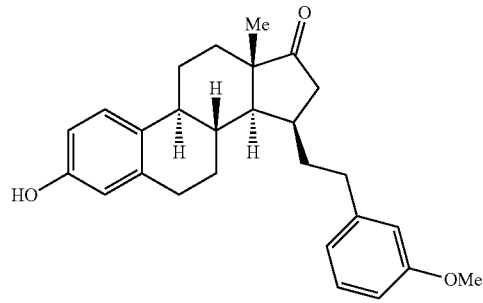

(10)

Compound 10 was prepared according to the above general procedure by reacting vinylestrone 2 with 3-methoxystyrene (66 µl). Chromatography on HPLC (30/70 MeCN/H$_2$O, $t_R$=16 min) yielded 52 mg of colorless solid 10: mp 178° C.; [α]$_D$+58.3 (c 1.706; CHCl$_3$); $^1$H NMR (500 MHz, CDCl$_3$) δ 1.03 (s, 3H, H-18), 1.36-1.50 (m, 2H, H-7a, 12a), 1.50 (m, 1H, H-11a), 1.61-1.76 (m, 3H, H-1a', 8, 14), 1.86-1.96 (m, 3H, H-1b, 7b, 12b), 2.25 (m, 1H, H-9), 2.23-2.38 (m, 2H, H-11b, 15), 2.40 (dd, 1H, J=19.4; 2.8 Hz, H-16a), 2.46 (dd, 1H, J=19.4; 8.1 Hz, H-16b), 2.51 (ddd, 1H, J=13.8; 9.1; 7.1 Hz, H-2a'), 2.73 (ddd, 1H, J=13.7; 9.7; 5.3 Hz, H-2b'), 2.80-2.93 (m, 2H, H-6), 3.81 (s, 3H, OCH$_3$), 5.00 (bs, 1H, OH), 6.59 (bd, 1H, J=2.8 Hz, H-4), 6.64 (ddm, 1H, J=8.4; 2.8 Hz, H-2), 6.73 (bdd, 1H, J=2.6; 1.6 Hz H-2"), 6.76 (ddd, 1H, J=8.2; 2.6; 1.0 Hz, H-4"), 6.78 (ddd, 1H, J=7.5; 1.6; 1.0 Hz, H-6"), 7.13 (dd, 1H, J=8.5; 1.1 Hz, H-1), 7.22 (bt, 1H, J=7.8 Hz, H-5"); $^{13}$C NMR (150.9 MHz, CDCl$_3$) δ 17.70 (C-18), 25.46 (C-11), 26.58 (C-7), 29.29 (C-6), 32.91 (C-1'), 33.72 (C-15), 33.80 (C-12), 35.81 (C-2'), 35.90 (C-8), 42.68 (C-16), 44.47 (C-9), 47.21 (C-13), 52.74 (C-14), 55.16 (OCH$_3$), 111.03 (C-4"), 112.70 (C-2), 114.41 (C-2"), 115.22 (C-4), 120.83 (C-6"), 126.15 (C-1), 129.44 (C-5"), 132.24 (C-10), 137.96 (C-5), 143.29 (C-1"), 153.59 (C-3), 159.64 (C-3"), 221.54 (C-17); IR (CHCl$_3$) ν 3598, 1729, 1611, 1602, 1594, 1585, 1500, 1489, 1439, 1281, 1259, 1233, 1191, 1165, 1153, 1017, 616 cm$^{-1}$; HR-MS (APCI) calculated $C_{27}H_{33}O_3$[M+H$^+$] 405.24242 found 405.24247. $R_f$ (4/1 hexane/EtOAc)=0.3.

Example 11: 3-Hydroxy-15β-(3,4-dimethoxyphenethyl)-estra-1,3,5(10)-trien-17-one (11)

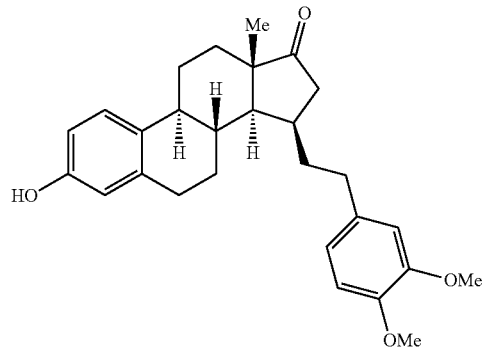

(11)

Compound 11 was prepared according to the above general procedure by reacting vinylestrone 2 with 3,4-dimethoxystyrene (72 µl). Chromatography on HPLC (30/70 MeCN/H$_2$O, t$_R$=14 min) yielded 17 mg of colorless solid 11: mp 146° C.; [α]$_D$+55.3 (c 0.347; CHCl$_3$); $^1$H NMR (500 MHz, CDCl$_3$) δ 1.03 (s, 3H, H-18), 1.31-1.56 (m, 3H, H-7a, 11a, 12a), 1.60-1.77 (m, 3H, H-1a', 8, 14), 1.85-1.95 (m, 3H, H-1b, 7b, 12b), 2.25 (m, 1H, H-9), 2.28-2.38 (m, 2H, H-11b, 15), 2.37-2.52 (m, 3H, H-16, H-2a'), 2.71 (ddd, 1H, J=13.8; 9.3; 5.2 Hz, H-2b'), 2.78-2.92 (m, 2H, H-6), 3.86 (s, 3H, OCH$_3$), 3.88 (s, 3H, OCH$_3$), 5.62 (bs, 1H, OH), 6.60 (bdm, 1H, J=2.8 Hz, H-4), 6.65 (bdd, 1H, J=8.5, 2.8 Hz, H-2), 6.70 (d, 1H, J=2.0 Hz, H-2"), 6.72 (dd, 1H, J=8.1; 2.8 Hz, H-6"), 6.81 (d, 1H, J=8.1 Hz, H-5"), 7.12 (bd, 1H, J=8.5 Hz, H-1); $^{13}$C NMR (150.9 MHz, CDCl$_3$) δ 17.69 (C-18), 25.41 (C-11), 26.56 (C-7), 29.25 (C-6), 33.03 (C-1'), 33.49 (C-15), 33.75 (C-12), 35.20 (C-2'), 35.87 (C-8), 42.64 (C-16), 44.40 (C-9), 47.22 (C-13), 52.67 (C-14), 55.80 (OCH$_3$), 55.87 (OCH$_3$), 111.19 (C-5"), 111.62 (C-2"), 112.73 (C-2), 115.22 (C-4), 120.29 (C-6"), 126.06 (C-1), 131.98 (C-10), 134.17 (C-1"), 137.79 (C-5), 147.24 (C-4"), 148.79 (C-3"), 153.79 (C-3), 221.87 (C-17); IR (CHCl$_3$) ν 3598, 2839, 1610, 1591, 1516, 1501, 1454, 1442, 1260, 1193, 1155, 1029, 870, 808, 581, 544 cm$^{-1}$; HR-MS (APCI) calculated C$_{34}$H$_{47}$O$_4$Si [M+Si] 547.32381 found 547.32368. R$_f$(4/1 hexane/EtOAc)=0.25.

Example 12: 15β-(4-Ethoxyphenethyl)-3-hydroxy-estra-1,3,5(10)-trien-17-one (12)

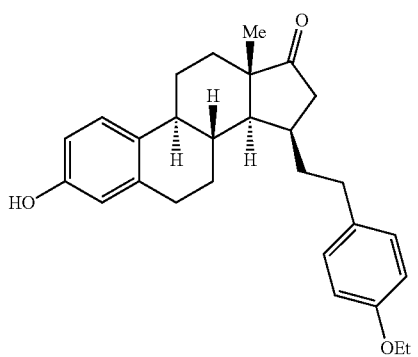

(12)

Compound 12 was prepared according to the above general procedure by reacting vinylestrone 2 with 4-ethoxystyrene (73 µl). Chromatography on HPLC (30/70 MeCN/H$_2$O, t$_R$=17 min) yielded 62 mg of colorless solid 12: mp 173° C.; [α]$_D$+62.5 (c 0.208; CHCl$_3$); $^1$H NMR (500 MHz, CDCl$_3$) δ 1.02 (s, 3H, H-18), 1.35-1.49 (m, 2H, H-7a, 12a), 1.41 (t, 3H, J=7.0 Hz, OCH$_2$CH$_3$), 1.50 (m, 1H, H-11a), 1.58-1.75 (m, 3H, H-1'a, 8, 14), 1.84-1.93 (m, 3H, H-1'b, 7b, 12b), 2.25 (m, 1H, H-9), 2.28-2.37 (m, 2H, H-11b, 15), 2.39 (dd, 1H, J=19.4, 2.8 Hz, H-16a), 2.44 (dd, 1H, J=19.4; 8.1 Hz, H-16b), 2.47 (ddd, 1H, J=13.8; 9.0; 7.1 Hz, H-2'a), 2.69 (ddd, 1H, J=13.8; 9.6; 5.3 Hz, H-2'b), 2.78-2.93 (m, 2H, H-6), 4.02 (q, 2H, OCH$_2$CH$_3$), 4.83 (bs, 1H, OH), 6.59 (bdt, 1H, J=2.8; 1.0; 1.0 Hz, H-4), 6.63 (bdd, 1H, J=8.4; 2.8 Hz, H-2), 6.83 (m, 2H, H-3"), 7.08 (m, 2H, H-2"), 7.13 (dd, 1H, J=8.5; 1.1 Hz, H-1); $^{13}$C NMR (150.9 MHz, CDCl$_3$) δ 14.87 (OCH$_2$CH$_3$), 17.70 (C-18), 25.48 (C-11), 26.57 (C-7), 29.32 (C-6), 33.25 (C-1'), 33.63 (C-15), 33.82 (C-12), 34.86 (C-2'), 35.91 (C-8), 42.72 (C-16), 44.48 (C-9), 47.20 (C-13), 52.77 (C-14), 63.42 (OCH$_2$CH$_3$), 112.69 (C-2), 114.44 (C-3"), 115.22 (C-4), 126.16 (C-1), 129.28 (C-2"), 132.33 (C-10), 133.55 (C-1"), 138.01 (C-5), 153.54 (C-3), 157.23 (C-4"), 221.46 (C-17); IR (CHCl$_3$) ν 3598, 3098, 3060, 1729, 1611, 1583, 1512, 1502, 1453, 1441, 1245, 1042 cm$^{-1}$; HR-MS (APCI) calculated C$_{28}$H$_{35}$O$_3$ [M+H$^+$] 419.25807 found 419.25810. R$_f$ (4/1 hexane/EtOAc)=0.3.

Example 13: 15β-(4-t-Butoxyphenethyl)-3-hydroxy-estra-1,3,5(10)-trien-17-one (13)

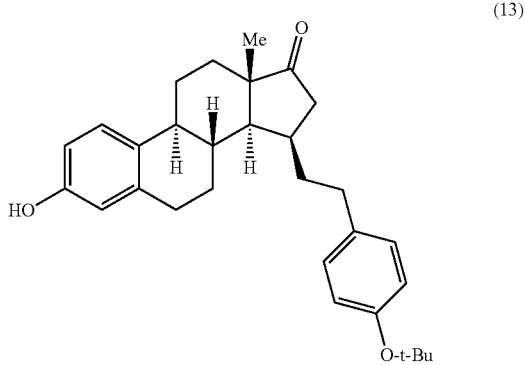

(13)

Compound 13 was prepared according to the above general procedure by reacting vinylestrone 2 with 4-t-butoxystyrene (92 µl). Chromatography on HPLC (30/70 MeCN/H$_2$O, t$_R$=17 min) yielded 94 mg of colorless solid 13: mp 192° C.; [α]$_D$+62.5 (c 0.208; CHCl$_3$); $^1$H NMR (500 MHz, CDCl$_3$) δ 1.02 (s, 3H, H-18), 1.35-1.49 (m, 2H, H-7a, 12a), 1.41 (t, 3H, J=7.0 Hz, OCH$_2$CH$_3$), 1.50 (m, 1H, H-11a), 1.58-1.75 (m, 3H, H-1'a, 8, 14), 1.84-1.93 (m, 3H, H-1'b, 7b, 12b), 2.25 (m, 1H, H-9), 2.28-2.37 (m, 2H, H-11b, 15), 2.39 (dd, 1H, J=19.4; 2.8 Hz, H-16a), 2.44 (dd, 1H, J=19.4; 8.1 Hz, H-16b), 2.47 (ddd, 1H, J=13.8; 9.0; 7.1 Hz, H-2'a), 2.69 (ddd, 1H, J=13.8; 9.6; 5.3 Hz, H-2'b), 2.78-2.93 (m, 2H, H-6), 4.02 (q, 2H, OCH$_2$CH$_3$), 4.83 (bs, 1H, OH), 6.59 (bdt, 1H, J=2.8; 1.0; 1.0 Hz, H-4), 6.63 (bdd, 1H, J=8.4; 2.8 Hz, H-2), 6.83 (m, 2H, H-3"), 7.08 (m, 2H, H-2"), 7.13 (dd, 1H, J=8.5; 1.1 Hz, H-1); $^{13}$C NMR (150.9 MHz, CDCl$_3$) δ 14.87 (OCH$_2$CH$_3$), 17.70 (C-18), 25.48 (C-11), 26.57 (C-7), 29.32 (C-6), 33.25 (C-1'), 33.63 (C-15), 33.82 (C-12), 34.86 (C-2'), 35.91 (C-8), 42.72 (C-16), 44.48 (C-9), 47.20 (C-13), 52.77 (C-14), 63.42 (OCH$_2$CH$_3$), 112.69 (C-2), 114.44 (C-3"), 115.22 (C-4), 126.16 (C-1), 129.28 (C-2"), 132.33 (C-10), 133.55 (C-1"), 138.01 (C-5), 153.54 (C-3), 157.23 (C-4"), 221.46 (C-17); IR (CHCl$_3$) ν 3598, 3098, 3060, 1729, 1611, 1583, 1512, 1502, 1453, 1441, 1245, 1042 cm$^{-1}$; HR-MS (APCI) calculated C$_{28}$H$_{35}$O$_3$ [M+H$^+$] 419.25807 found 419.25810. R$_f$ (4/1 hexane/EtOAc)=0.3.

Example 14: 15β-(4-Hydroxyphenethyl)-3-hydroxy-estra-1,3,5(10)-trien-17-one (14)

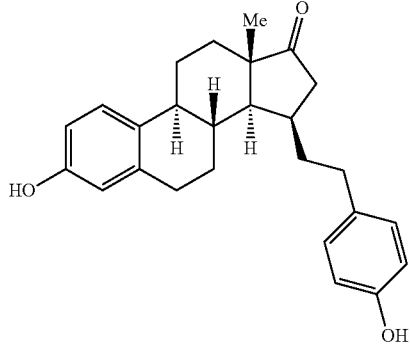

(14)

Compound 14 was prepared according to the above general procedure by reacting vinylestrone 2 with 4-acetoxystyrene (75 µl). Resulting (3-(Hydroxy)-estra-1,3,5(10)-trien-17-one-15β-yl)ethenyl)phenyl-acetate was further dissolved in methanol and catalytical amount of freshly prepared solution of 1 mol·l$^{-1}$ CH$_3$ONa in methanol was added at room temperature. After 3 h, DOWEX® 50W (H+, ion exchange resin) was added until the pH of the mixture reached 5-6. Then the resin was filtered off, solvent was removed under reduced pressure and the residue was purified by chromatography on HPLC (30/70 MeCN/H$_2$O, t$_R$=12 min) yielded 37 mg of colorless solid 14: mp 169° C.; [α]$_D$+79.1 (c 0.283; CH$_3$OH); $^1$H NMR (500 MHz, MeOD) δ 0.99 (s, 3H, H-18), 1.29 (s, 1H, H-7a), 1.34-1.47 (m, 2H, 11a, 12a), 1.57-1.68 (m, 3H, H-1', 8, 14), 1.75-1.89 (m, 3H, H-1'b, 7b, 12b), 2.17 (m, 1H, H-9), 2.25-2.33 (m, 2H, H-11b, 15), 2.34-2.40 (m, 2H, H-16), 2.42 (dt, 1H, J=13.6, 7.9 Hz, H-2'a), 2.66 (ddd, 1H, J=13.6; 8.5; 5.4 Hz, H-2'b), 2.74-2.80 (m, 2H, H-6), 6.49 (dm, 1H, J=2.7 Hz, H-4), 6.53 (bdd, 1H, J=8.5; 2.7 Hz, H-2), 6.71 (m, 2H, H-3''), 7.00 (m, 2H, H-2''), 7.04 (dd, 1H, J=8.5; 1.1 Hz, H-1); $^{13}$C NMR (150.9 MHz, MeOD) δ 18.21 (C-18), 26.68 (C-11), 27.78 (C-7), 30.38 (C-6), 34.57 (C-15), 34.58 (C-1'), 35.09 (C-12), 35.69 (C-2'), 37.41 (C-8), 43.64 (C-16), 45.83 (C-9), 48.49 (C-13), 53.92 (C-14), 113.71 (C-2), 116.12 (C-4), 116.14 (C-3''), 126.91 (C-1), 130.54 (C-2''), 132.33 (C-1''), 134.00 (C-1''), 138.76 (C-5), 156.11 (C-3), 156.52 (C-4''), 224.20 (C-17); IR (KBr) ν 3370, 2926, 2855, 1716, 1612, 1583, 1514, 1450, 1441, 1376, 1356, 1217, 1170, 1099, 922, 827, 755, 731 cm$^{-1}$; HR-MS (APCI) calculated C$_{26}$H$_{31}$O$_3$ [M+H$^+$] 391.22677 found 391.22690. R$_f$(7/1 CHCl$_3$/MeOH)=0.3.

Example 15: 3-Hydroxy-15β-(4-methylphenethyl)-estra-1,3,5(10)-trien-17-one (15)

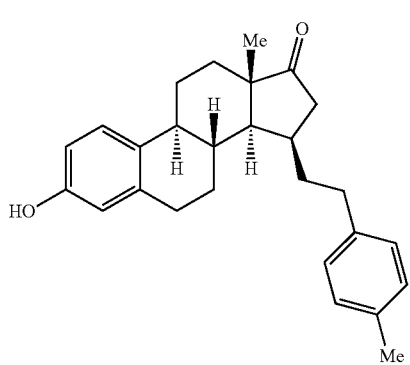

(15)

Compound 15 was prepared according to the above general procedure by reacting vinylestrone 2 with 4-methylstyrene (64 µl). Chromatography on HPLC (35/65 MeCN/H$_2$O, t$_R$=36 min) yielded 25 mg of colorless solid 15: mp 159° C.; [α]$_D$ −13.9 (c 0.170; CHCl$_3$); $^1$H NMR (500 MHz, CDCl$_3$) δ 1.02 (s, 3H, H-18), 1.36-1.55 (m, 3H, H-7a, 11a, 12a), 1.64 (dddd, 1H, J=13.6; 11.7; 9.2; 5.3 Hz, H-1'a), 1.66-1.76 (m, 2H, H-8, 14), 1.86-1.95 (m, 3H, H-1b', 7b, 12b), 2.25 (m, 1H, H-9), 2.33 (s, 3H, CH$_3$-Ph), 2.30-2.34 (m, 2H, H-11b, 15), 2.37-2.46 (m, 2H, H-16), 2.49 (ddd, 1H, J=13.7; 9.2; 6.9 Hz, H-1'a), 2.71 (ddd, 1H, J=13.7; 9.8; 5.3 Hz, H-1'b), 2.80-2.94 (m, 2H, H-6), 4.68 (s, 1H, OH), 6.59 (dm, 1H, J=2.8 Hz, H-4), 6.63 (dd, 1H, J=8.5; 2.8 Hz, H-2), 7.07 (m, 2H, H-2''), 7.11 (m, 2H, H-3''), 7.13 (dd, 1H, J=8.5; 1.0 Hz, H-1); $^{13}$C NMR (150.9 MHz, CDCl$_3$) δ 17.73 (C-18), 21.01 (CH$_3$-Ph), 25.51 (C-11), 26.62 (C-7), 29.34 (C-6), 33.22 (C-1'), 33.81 (C-15), 33.85 (C-12), 35.40 (C-2'), 35.95 (C-8), 42.72 (C-16), 44.52 (C-9), 47.20 (C-13), 52.81 (C-14), 112.71 (C-2), 115.23 (C-4), 126.20 (C-1), 128.29 (C-2''), 129.15 (C-3''), 132.41 (C-10), 135.54 (C-4''), 138.05 (C-5), 138.58 (C-1''), 153.51 (C-3), 221.34 (C-17); IR (KBr) ν 3382, 1734, 1719, 1584, 1514, 1501, 1443, 708 cm$^{-1}$; HR-MS (APCI) calculated C$_{27}$H$_{33}$O$_2$ [M+H$^+$] 389.24751 found 389.24751. R$_f$ (4/1 hexane/EtOAc)=0.3.

Example 16: 15β-(3,4,5-Trifluorophenethyl)-3-hydroxy-estra-1,3,5(10)-trien-17-one (16)

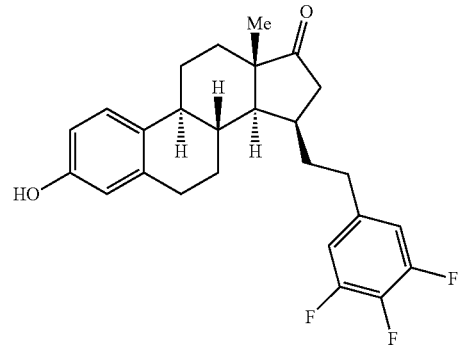

(16)

Compound 16 was prepared according to the above general procedure by reacting vinylestrone 2 with 3,4,5-trifluorostyrene (77 mg). Chromatography on HPLC (30/70 MeCN/H$_2$O, t$_R$=21 min) yielded 8 mg of colorless solid 16: mp 182° C.; [α]$_D$+48.3 (c 0.118; CHCl$_3$); $^1$H NMR (500 MHz, CDCl$_3$) δ 1.03 (s, 3H, H-18), 1.39-1.56 (m, 3H, H-7a, 11a, 12a), 1.57-1.77 (m, 3H, H-1 'a, 8, 14), 1.81-1.96 (m, 3H, H-1'b, 7b, 12b), 2.21-2.40 (m, 3H, H-11b, 9, 15), 2.36 (dd, 1H, J=19.3; 2.2 Hz, H-16a), 2.46 (dd, 1H, J=19.3; 8.9 Hz, H-16b), 2.48 (ddd, 1H, J=14.0; 9.3; 7.0 Hz, H-2'a), 2.69 (ddd, 1H, J=14.0; 9.7; 5.1 Hz, H-2'b), 2.82-2.95 (m, 2H, H-6), 4.86 (bs, 1H, OH), 6.60 (d, 1H, J=2.8 Hz, H-4), 6.64 (dd, 1H, J=8.4; 2.7 Hz, H-2), 6.78 (m, 2H, H-2''), 7.13 (bd, 1H, J=8.4 Hz, H-1); $^{13}$C NMR (150.9 MHz, CDCl$_3$) δ 17.73 (C-18), 25.41 (C-11), 26.66 (C-7), 29.20 (C-6), 32.60 (C-1'), 33.56 (C-15), 33.79 (C-12), 35.08 (C-2'), 35.86 (C-8), 42.43 (C-16), 44.42 (C-9), 47.16 (C-13), 52.65 (C-14), 112.19 (dd, J$^{C-F}$=15.9; 4.7 Hz, C-2''), 112.78 (C-2), 115.23 (C-4), 126.14 (C-1), 132.14 (C-10), 137.77 (C-1''), 137.82 (C-5), 138.16 (dt, J$^{C-F}$=249.4; 15.2 Hz, C-4''), 151.10 (ddd, J$^{C-F}$=249.6; 9.8; 3.9 Hz, C-3''), 153.65 (C-3), 220.74 (C-17); $^{19}$F NMR (470.3 MHz, CDCl$_3$) δ −160.47 (t, 1F, $J^{F-F}$=20.5 Hz), −131.13 (d, 2F, $J^{F-F}$=20.5 Hz); IR (KBr) ν 3295, 1718, 1620, 1585, 1529, 1501, 1376 cm$^{-1}$; HR-MS (APCI) calculated C$_{26}$H$_{28}$O$_2$F$_3$ [M+H$^+$] 429.20259 found 429.20349. R$_f$ (4/1 hexane/EtOAc)=0.3.

Example 17: 15β-(2,3,4,5,6-Pentafluorophenethyl)-3-hydroxy-estra-1,3,5(10)-trien-17-one (17)

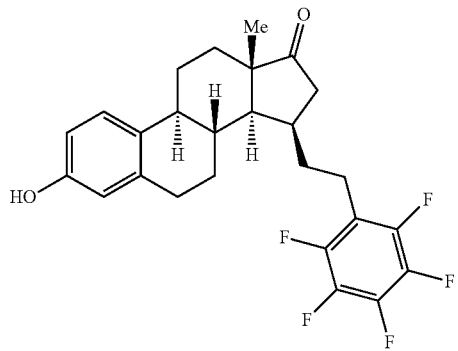

(17)

Compound 17 was prepared according to the above general procedure by reacting vinylestrone 2 with 2,3,4,5,6-pentafluorstyrene (67 µl). Chromatography on HPLC (30/70 MeCN/H$_2$O, t$_R$=42 min) yielded 27 mg of colorless solid 17: mp 151° C.; [α]$_D$+43.7 (c 0.544; CHCl$_3$); $^1$H NMR (500 MHz, CDCl$_3$) δ 1.00 (s, 3H, H-18), 1.41-1.55 (m, 3H, H-7a, 11a, 12a), 1.61 (m, 1H, H-1a'), 1.69 (m, 1H, H-8), 1.74 (m, 1H, H-14), 1.85-1.95 (m, 3H, H-1b', 7b, 12b), 2.27 (m, 1H, H-9), 2.30-2.39 (m, 2H, H-11b, 15), 2.43 (dd, 1H, J=19.4; 2.4 Hz, H-16a), 2.51 (dd, 1H, J=19.4, 8.6 Hz, H-16b), 2.67 (m, 1H, H-2a'), 2.79 (m, 1H, H-2b'), 2.83-2.96 (m, 2H, H-6), 4.93 (bs, 1H, OH), 6.60 (bd, 1H, J=2.8 Hz, H-4), 6.64 (dd, 1H, J=8.4; 2.8 Hz, H-2), 7.13 (bd, 1H, J=8.4 Hz, H-1); $^{13}$C NMR (150.9 MHz, CDCl$_3$) δ 17.63 (C-18), 22.19 (C-2'), 25.43 (C-11), 26.56 (C-7), 29.19 (C-6), 30.80 (C-1'), 33.74 (C-12), 33.96 (C-15), 35.86 (C-8), 42.34 (C-16), 44.40 (C-9), 47.12 (C-13), 52.61 (C-14), 112.77 (C-2), 114.44 (bt, $J^{C-F}$=18.8 Hz, C-1''), 115.23 (C-4), 126.16 (C-1), 132.10 (C-10), 137.46 (dm, $J^{C-F}$=250.4 Hz, C-3''), 137.87 (C-5), 139.68 (dm, $J^{C-F}$=251.7 Hz, C-4''), 144.97 (dm, $J^{C-F}$=243.2 Hz, C-2''), 153.63 (C-3), 220.53 (C-17); $^{19}$F NMR (470.3 MHz, CDCl$_3$) δ−158.78 (m, 2F, F-3''), −153.61 (t, 1F, F-4''), −141.15 (m, 2F, F-2''); IR (CHCl$_3$) ν 3599, 1732, 1657, 1611, 1585, 1521, 1504, 1440, 1378, 1122, 1068, 963 cm$^{-1}$; HR-MS (APCI) calculated C$_{26}$H$_{26}$O$_2$F$_5$ [M+H$^+$] 465.18475 found 465.18468. R$_f$ (4/1 hexane/EtOAc)=0.3.

Example 18: 3-Hydroxy-15β-vinyl-estra-1,3,5(10)-trien-17-one (2a)

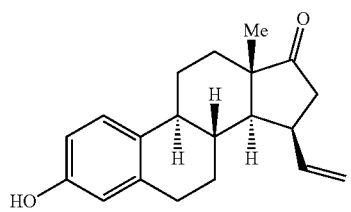

(2a)

Reaction of protected vinylestrone 2 (55 mg, 0.134 mmol) according to the general procedure yielded vinylestrone 18 (38 mg, 95%) as a colorless solid: mp 162° C.; [α]$_D$+79.4 (c 0.175, CHCl$_3$); $^1$H NMR (500 MHz, CD$_2$Cl$_2$) δ 1.01 (s, 3H), 1.34-1.61 (m, 3H), 1.72-1.73 (m, 2H), 2.13-2.19 (m, 2H), 2.28 (m, 1H), 2.36 (m, 1H), 2.52 (dd, J=19.5, 9.0 Hz, 1H), 2.63 (dd, J=19.5, 2.2 Hz, 1H), 2.83-2.90 (m, 2H), 3.02-3.26 (m, 1H), 4.69 (s, 1H), 5.02-5.27 (m, 2H), 6.14 (ddd, J=17.2, 10.4, 6.7 Hz, 1H), 6.48-6.69 (m, 2H), 7.14 (d, J=8.4 Hz, 1H); $^{13}$C NMR (150.9 MHz, CD$_2$Cl$_2$) δ 16.90, 25.49, 26.33, 29.25, 33.40, 35.96, 37.15, 41.75, 44.50, 47.69, 52.69, 115.96, 117.24, 119.98, 125.85, 132.63, 137.62, 139.00, 156.54, 221.20; IR (CHCl$_3$) ν 3599, 3400, 3319, 3082, 2938, 2863, 2843, 1731, 1640, 1611, 1585, 1501, 1440, 1377, 1272, 1248, 1190, 1165, 1101, 998, 918, 690, 577, 587, 445 cm$^1$; HR-MS (ESI) for C$_{20}$H$_{24}$O$_2$Na [M+Na$^+$] calculated 319.16685, found 319.16703. R$_f$ (4/1 hexane/EtOAc)=0.3.

Biological Tests

Example 19: Inhibition of the Enzyme Activity of 17βHSDs by 15-Substituted Estrone Derivatives The inhibitory activity of the test substances was determined for individual isoenzymes from the 17βHSD family, specifically these were the types 1, 2, 3, 4, 5 and 7. *Escherichia coli* and mammalian cells expression systems were used for recombinant expression of individual isozymes of human 17βHSD. Only in the case of 17HSD5 the enzyme was partially purified and supernatant obtained by centrifugation of the bacterial lysate was used for testing. Systems expressing specific 17βHSD type were suspended in a reaction buffer and incubated with tritium-labeled substrates and respective cofactors at 37° C. in two parallel tests: the control arrangement (DMSO without the inhibitor) and the test arrangement (DMSO with the inhibitor). DMSO serves as a negative control in this case. After 20-30% of the substrate was converted by the activity of the enzyme to the product in a control test, both tests were terminated. Substrate and product from the test arrangement were isolated by SPE (solid phase extraction), and then separated by reverse phase HPLC. Substrate conversion was determined by integration of the signals of the substrate and product, and was expressed in %. For the purposes of the subsequent calculation of enzyme inhibition, the conversion of the control test was designated as 0% inhibition. All tests were performed in triplicates. IC$_{50}$ values were subsequently determined by a standard method using the "One Ligand Binding" model of SigmaPlot kinetics module (Schustera et. al. *J. Ster. Biochem. Mol. Biol.* 2011, 125, 148; Möller et. al. *Biioorg. Med. Chem. Lett.* 2009, 19, 6740; Möller et. al. *PLoS One,* 2010, 5, 6, e10969).

The inhibitory activities of the tested estrone derivatives at various concentrations on human 17βHSD type 1 are summarized in Table 1. The tested compounds showed high inhibitory activity against human 17βHSD type 1 already at 0.1 µmol l$^{-1}$ concentration. Two of the most effective derivatives, compound 6 and 9, are highlighted in Table 1.

Many of the substances are effective also on 17βHSD type 5 (Table 1). The activities of the other isozymes examined—namely 17βHSD type 2, 3, 4 and 7—were barely reduced by the presence of the substances, even at concentrations of 10 µmol l$^{-1}$ (inhibition never higher than 50%, data not shown). The tested compounds are therefore selective inhibitors of 17βHSD1 and in some cases additionally of 17βHSD5.

Compound 2a inhibits exclusively the 17βHSD1 isoenzyme; however, at the same time it shows also a partial estrogenicity.

TABLE 1

Inhibitory activity of selected 15-substituted estrone derivatives (expressed in % of inhibition of human 17βHSD types 1 and 5 at various concentrations of test substances).

| Compound No. | 17βHSD1 $0.1$ $\mu mol \cdot l^{-1}$ | 17βHSD1 $1$ $\mu mol \cdot l^{-1}$ | 17βHSD1 $IC_{50}$ $(nmol \cdot l^{-1})$ | 17βHSD5 $1$ $\mu mol \cdot l^{-1}$ |
|---|---|---|---|---|
| 2a | 79 | 95 | 17 | 7 |
| 3 | 66 | 83 | 50 | 60 |
| 4 | 68 | 91 | 42 | 89 |
| 5 | 72 | 92 | 55 | 70 |
| 6 | 90 | 97 | 9 | 90 |
| 7 | 84 | 99 | 16 | 63 |
| 8 | 77 | 92 | 18 | 76 |
| 9 | 91 | 100 | 10 | 91 |
| 10 | 72 | 87 | N/A | N/A |
| 11 | 36 | 67 | N/A | N/A |
| 12 | 85 | 88 | N/A | 80 |
| 13 | 62 | 80 | N/A | N/A |
| 14 | 72 | 97 | N/A | 42 |
| 15 | 87 | 100 | 8 | 86 |
| 16 | 67 | 95 | 36 | 79 |
| 17 | 56 | 90 | N/A | 31. |

N/A: not determined;
No.: number of derivative.

Example 20: Determination of the Activity of Compounds on Steroid Receptors ERα, AR and PR in Cell Luciferase Reporter Assays Effect of newly prepared substances on the activity of steroid receptors, estrogen receptor α (ERα) and androgen receptor (AR) and progesterone receptor (PR) was assessed in vitro by selective luciferase reporter assays based on cell reporter lines for ERα, AR and PR in U2OS cells (Sedlák et al. *Comb. Chem. High T. Scr.* 2011, 14, 248). These cell lines were prepared by introducing an expression vector with coding sequence for a particular human steroid receptor and reporter vector pGL4 (Promega, USA) containing responsive elements for a specific steroid receptor in a promoter regulating the expression of luciferase gene. Cells that stably integrated both vectors into the genome were isolated on selection medium containing hygromycin and G418 (Geneticin® aminoglycoside). From these selected cell cultures, clones of cells were further isolated, showing an optimal response in assays with reference ligands for the steroid receptor.

U2OS reporter lines were grown in DMEM (Thermo Fisher Scientific, catalog number 11880-036), without phenol red supplemented with 10% FBS (Thermo Fisher Scientific, catalog number 10270-106), 2 mmol·l$^{-1}$ Glutamax-1 (Thermo Fisher Scientific, catalog number 35050061) and a solution of penicillin and streptomycin (Thermo Fisher Scientific, catalog number 15070063). Cells were incubated with 5% $CO_2$ at 37° C. Two days prior to testing of compounds, growth medium was changed to DMEM without phenol red, supplemented with 2 mmol·l$^{-1}$ Glutamax and 4% FBS depleted of lipophilic components (including the endogenous ligands of steroid receptors) (Hyclone, GE Healthcare Life Sciences, USA). Two days after the medium replacement, the cells were harvested, counted and resuspended in a medium of the same composition at a concentration of $0.5 \times 10^6$/ml. The cell suspension was transferred in batches into 1536-well white plates adjusted for cultivation of adherent cells (Corning Inc., NY, USA). 4 μl of cell suspension equivalent to 2500 cells were transferred to each well. Test compounds were diluted in DMSO and transferred into wells to cells using the contactless acoustic dispenser Echo 520 (Labcyte). Testing was performed in 10 concentration points in the range 10 μmol·l$^{-1}$ to 1 nmol·l$^{-1}$ in triplicates.

The experiment was performed in two modes. Agonistic properties of test substances were determined in the agonistic mode; antagonistic properties were detected in the antagonistic mode. In the antagonist mode, 30 minutes after the transfer of the test substances, 0.5 μl of a solution of the agonist was added to the test samples. A solution of 1 nmol·l$^{-1}$ E2 was used for ERα, 1 nmol·l$^{-1}$ dihydrotestosterone (DHT) for AR and 1 nmol·l$^{-1}$ progesterone for PR. Growth medium for the cells was used to dissolve the compounds.

In order to distinguish between the specific, steroid hormone response elements-driven regulation of the luciferase expression and the possible effects of test compounds on the luciferase activity, compounds were tested in parallel experiment on a U2OS cell line constitutively expressing luciferase gene.

Luciferase activity was determined by a commercial kit Britelite plus a luciferase reporter gene assay reagent (Perkin Elmer, USA), 24 h after addition of compounds to cells. The intensity of luminescence was measured on an Envision multimode spectrophotometer (PerkinElmer).

To the extent of considered therapeutic concentrations, the compounds have no estrogenic effect. Selected compounds exhibit even features of ER/AR antagonists. Compounds 3, 4 and 7 are ER antagonist; Compound 9 is an AR antagonist and Compounds 11, 12 and 13 are antagonists of both types of receptors (ER and AR).

This cytotoxicity test was performed for all the prepared compounds, and the results showed that none of the derivatives prepared exhibits cytotoxic effect up to a concentration of 20 μmol·l$^{-1}$ of the test compounds.

Compounds 9 and 12 were further tested in extended concentration range from 100 μmol·l$^{-1}$ to 0.01 nmol·l$^{-1}$ and data are summarized in Table 2. Both compounds show weak partial agonistic properties starting at 10 μmol·l$^{-1}$ on ERα. The agonistic effects are unique to ERα and are not observed on other steroid receptors: AR and PR. The activation of ERα is only partial and the efficacy is below 40% of the maximal effect produced by E2. At even higher concentrations (10-100 μmol·l$^{-1}$), compounds exhibit antagonistic activities mainly on ERα and PR and to a lesser extent on AR too. The antagonist activities are not accompanied with luciferase inhibition or cell toxicity. Considering that compounds effectively inhibit 17βHSD1 at 0.01 μmol·l$^{-1}$, interactions with steroid receptors occur at considerably higher concentrations (>10 μmol·l$^{-1}$) and do not interfere with 17βHSD mediated effects. Moreover, antagonist activities on ERα, PR and AR are desirable in case compounds are used to block proliferation of ER/AR positive breast/prostate cancer cells where the proliferation is driven by steroid receptors.

TABLE 2

In vitro testing of the compounds in ERα, AR and PR cell-based reporter assays
($EC_{50}/IC_{50}$, µmol · l$^{-1}$).

| Compound No. | AGONIST mode ERα | AR | PR | ANTAGONIST mode ERα | AR | PR | Luciferase activity | Cell viability |
|---|---|---|---|---|---|---|---|---|
| 9 | >10 | n.a. | n.a. | 23.46 | n.a. | 13.60 | n.a. | >100.00 |
| 12 | >10 | n.a. | n.a. | 28.97 | 89.09 | 13.65 | n.a. | >100.00 |
| E2 | $6.0 \times 10^{-5}$ | — | — | — | — | — | — | — |
| DHT | — | $2.0 \times 10^{-4}$ | — | — | — | — | — | — |
| P4 | — | — | $3.6 \times 10^{-3}$ | — | — | — | — | — |
| 4-OHT | — | — | — | 0.03 | — | — | 10.15 | 11.98 |
| Enzalutamide | — | — | — | — | 6.68 | — | n.a. | 89.43 |
| RU486 | — | — | — | — | — | <0.003 | 17.90 | 47.69 | n.a.: not active.

Example 21: Compound-Mediated Inhibition of E1 Induced Proliferation of Triple Positive Breast Cancer Cell Line T47D Triple positive breast cancer cell line T47D has several features that make it a unique model for study of the biological function of 17βHSD1 and of the clinical potential of 17βHSD1 inhibitors. T47D cells express high levels of ERα, PR and 17βHSD1 and cell growth is estrogen-dependent. In the absence of estrogens, proliferation rate slows down considerably and cells stop dividing eventually. Estrogens can be supplied directly, by adding E2 to the growth medium. E2 promotes T47D cell proliferation by directly activating ERα. Alternatively, cell proliferation can be induced by suppling the estrogenic precursor, E1, which is transformed by 17βHSD1 expressed by cells, to E2.

In this study, T47D cells were propagated in RPMI 1640 medium supplemented with 10% fetal bovine serum, 2 mmol·l$^{-1}$ glutaMAX (Thermo Fisher Scientific, MA, USA), and penicillin/streptomycin (Thermo Fisher Scientific, Waltham, USA) and incubated in a 5% CO2-humidified atmosphere at 37° C. to the amount needed for the experiment. Two days prior to testing of compounds, growth medium was changed to medium without phenol red, supplemented with 2 mmol·l$^{-1}$ Glutamax and 4% FBS depleted of lipophilic components (including the endogenous estrogenic substances) (Hyclone, GE Healthcare Life Sciences, USA). Two days after the medium replacement, the cells were harvested, counted and resuspended in a medium. Cells were dispensed with liquid dispenser Multi-drop (Thermo Fisher Scientific, Waltham, USA), to the cell culture treated, 12-well plates (Corning Inc., NY, USA) at 100 000 cells/well in 1 mL of total media volume. Compounds diluted in the medium were added 24 h later and cells were incubated for 7 more days with or without 1 µmol·l$^{-1}$ E1. Growth medium was changed during the experiment on day 3, and freshly diluted compounds were added to cells again. After 7 days of cell cultivation with compounds, cells were harvested and counted. Cell number was normalized and 100% was attributed to cells cultivated in the presence of 1 µmol·l$^{-1}$ E1 and 0% to the cells cultivated without any added compound.

Figure 1:
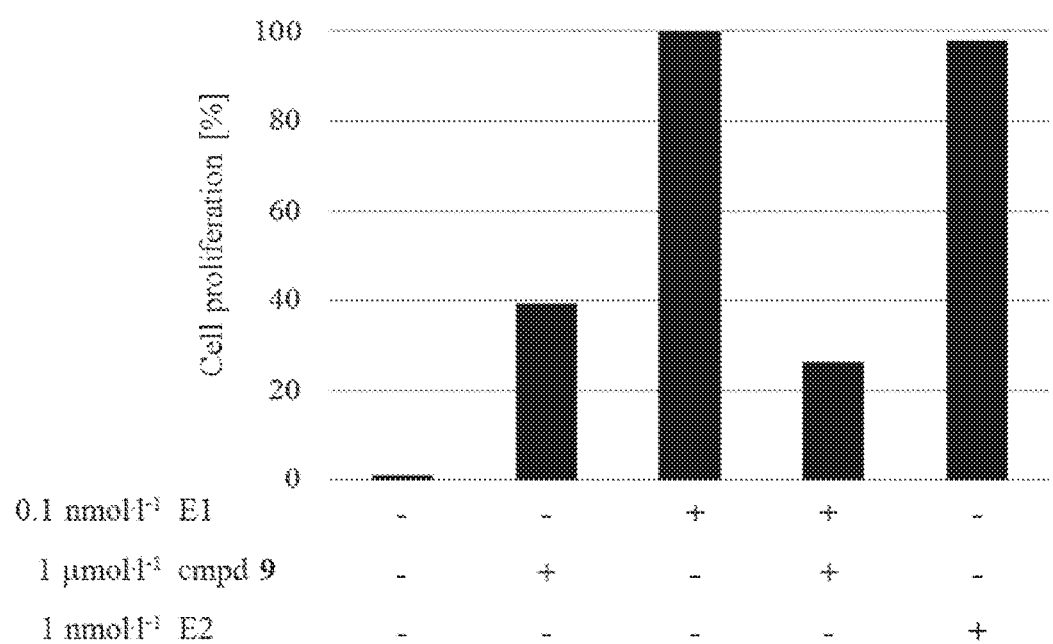
FIG. 1 shows that compound 9 blocks E1-induced proliferation of T47D breast cancer cells after 7 days of cell cultivation with both compounds.

Results are summarized in FIG. 1. The data shows that both E1 and E2 promote strongly cell proliferation. Compound 9 is weakly pro-proliferative at 1 µmol·l$^{-1}$ when the cells are incubated with the compound alone. Compound 9 reverses the pro-proliferative activity of E1 when incubated together with 0.1 nmol·l$^{-1}$ E1, showing that inhibition of the enzymatic activity of 17βHSD1 can have desired biological activity: inhibition of proliferation of ER positive, breast cancer cells.

Example 22: Determination of Cytotoxicity of the Compounds in the U2OS Cell Line To separate the antagonist activity of test compounds from the cytotoxic effect on U2OS cells (cell line derived from osteosarcoma), an experiment for determination of cell viability was performed in parallel with the reporter assay. Original, genetically unmodified U2OS cells were grown under the same conditions as the reporter cells. These cells were further treated and incubated with the compounds in a completely identical manner and for the same time as cells in the reporter assay. At the end of the experiment, the amount of ATP was determined using BriteLite luciferase homogeneous assay as a measure of cell viability. The data were then processed together with data from the reporter assays.

This cytotoxicity test was performed for all the prepared compounds, and the results showed that none of the derivatives prepared exhibits cytotoxic effect up to a concentration of 20 µmol·l$^{1}$ of the tested compounds.

Example 23: Determination of Cytotoxicity of Compounds on Tumor and Non-Tumor Cells Compounds 5, 6, 7, 9, 14 and 15 were used for evaluation of antitumor activity. MTT cytotoxicity assay was used in vitro on cell lines derived from normal tissues and from tumors. Specifically, these were the K562 line (human myeloid leukemia), K562-Tax (human myeloid leukemia resistant to taxol and overexpressing PgP protein for multidrug resistance), CEM (T-lymphoblastic leukemia), CEM-DNR bulk (T-lymphoblastic leukemia resistant doxorubicin, lacking the expression of the target gene for inhibitors of topoisomerase II alpha), A549 line (human lung adenocarcinoma), HCT116p53 wt (human colon cancer), HCT116p53−/− (human colon cancer, mutant p53), U2OS line of human osteosarcoma and two fibroblast lines MRC5 and BJ as examples of non-tumor cells. Expression characteristics, profiles of susceptibility to classical antitumor drugs and methodology of the MTT cytotoxicity assay were repeatedly published (e.g. Noskova et al. *Neoplasma* 2002, 49, 418; Šarek et. al. *J. Med. Chem.* 2003, 46, 25, 5402).

Substances in the tests did not show significant cytotoxicity on tumor and non-tumor cell lines of various histogenetic origin, which indicates the absence of off-target antitumor effect. The test results are summarized in Table 3.

TABLE 3

In vitro cytotoxicity ($IC_{50}$, $\mu mol \cdot l^{-1}$) tested on cell lines of tumor and non-tumor origin.

| Compound No. | CEM $IC_{50}$ | σ | CEM-DNR-bulk $IC_{50}$ | σ | K562 $IC_{50}$ | Σ | K562-Tax $IC_{50}$ | σ | A549 $IC_{50}$ | σ |
|---|---|---|---|---|---|---|---|---|---|---|
| 5  | 25.16 | 3.80 | 28.24 | 1.79 | 25.25 | 4.68 | 19.31 | 2.44 | 35.76 | 4.48 |
| 6  | 16.34 | 0.90 | 24.61 | 2.29 | 26.89 | 4.88 | 13.21 | 1.72 | 35.75 | 3.48 |
| 7  | 25.56 | 4.97 | 32.81 | 3.78 | >50.00 | 0.00 | 12.49 | 2.76 | >50.00 | 0.00 |
| 9  | 21.36 | 3.53 | 22.14 | 3.48 | 27.70 | 5.71 | 9.12  | 0.96 | 40.98 | 3.48 |
| 14 | 25.81 | 3.63 | 30.76 | 2.85 | 22.60 | 3.20 | 18.89 | 1.59 | 41.32 | 3.33 |
| 15 | 21.67 | 2.82 | 24.10 | 1.95 | 23.80 | 3.25 | 13.80 | 1.73 | 28.21 | 3.90 |

| Compound No. | HCT116p53 wt $IC_{50}$ | σ | HCT116p53-/- $IC_{50}$ | σ | U2OS $IC_{50}$ | Σ | BJ $IC_{50}$ | σ | MRCS $IC_{50}$ | Σ |
|---|---|---|---|---|---|---|---|---|---|---|
| 5  | 29.19 | 3.33 | 30.47 | 2.73 | 30.38 | 3.70 | 24.26 | 2.89 | 18.37 | 3.11 |
| 6  | 29.34 | 1.97 | 30.80 | 2.13 | 27.88 | 3.18 | 28.81 | 3.76 | 21.00 | 1.83 |
| 7  | >50.00 | 0.00 | >50.00 | 0.00 | >50.00 | 0.00 | >50.00 | 0.00 | >50.00 | 0.00 |
| 9  | 29.38 | 3.33 | 35.73 | 0.54 | 45.32 | 2.86 | >50.00 | 0.00 | >50.00 | 0.00 |
| 14 | 28.22 | 2.90 | 32.57 | 2.14 | 44.59 | 4.38 | 50.00 | 0.00 | 50.00 | 0.00 |
| 15 | 28.27 | 1.50 | 29.35 | 1.88 | 28.90 | 2.34 | 27.93 | 1.62 | 19.55 | 3.58 |

σ: standard deviation.

Example 24: Determination of Long-Term Effects of Compounds on Breast, Prostate and Ovarian Cancer Cell Lines Compounds 9 and 12 were tested in the proliferation assay with cell lines derived from the triple negative breast cancer (MDA-MB-231), AR-negative prostate cancer (PC3, DU145) and ovarian cancer (SK-OV-3, CaoV-3). These cell lines do not express biologically significant level of endogenous 17βHSD1 and are not responsive to antihormone treatment. The experiment was carried out exactly as in the example 21. The cells were treated with 1 $\mu mol \cdot l^{-1}$ compounds for 7 days. At the end of the treatment, cells were harvested and counted. Cell number was normalized and 100% was attributed untreated cells, 0% to the sample with no cells.

Cultured cells show no cytotoxic or pro-proliferative effect when cultivated with 1 $\mu mol \cdot l^{-1}$ compounds for 7 days. The data prove that compounds have no effect on cells that are not dependent/sensitive to steroid hormones, and especially on the estradiol produced by the conversion of E1 to E2 by 17βHSD (Table 4).

TABLE 4

7 day proliferation assay with cell lines derived from breast, prostate and ovarian cancer. Values represent % of survived cells compared to untreated samples.

| Compound No. | Breast MDA-MB-231 | Prostate PC3 | Prostate DU145 | Ovary SK-OV-3 | Ovary CaOV-3 |
|---|---|---|---|---|---|
| 9  | 106 | 96 | 98 | 113 | 94 |
| 12 | 98  | 98 | 86 | 97  | 88 |

Example 25: Determination of the 17βHSD Inhibition in Cells In Vitro

The effect of compounds on the inhibition of 17βHSD in cell lines derived from hormonally active tumors MCF-7 (human breast carcinoma transfected with human 17βHSD1) and CHO (hamster ovarian carcinoma transfected with human 17βHSD1) was monitored through cumulation of 17βHSD precursor, hormone E1, in the supernatant of cell lines in a time interval of 8 and 24 hours. For this experiment, non-cytotoxic concentrations of estrone derivative (10 $\mu mol \cdot l^{-1}$) were used. E1 levels were determined by an immuno-enzymatic assay.

Addition of estrone derivatives to 17βHSD1 transfected cell cultures of hormonally active/dependent tumors in vitro led to significantly increased level of E1, which is a substrate to 17βHSD enzyme, within 8 hours. This observation is consistent with the inhibition of 17βHSD in vitro. Results of the analysis of 17βHSD inhibition in cell lines in vitro are summarized in Table 5.

TABLE 5

Results of the analysis of 17βHSD inhibition in cell lines in vitro

| | MCF-7 | | CHO | |
|---|---|---|---|---|
| No. | 8 hr. E1 (pg/ml) | 24 hr. E1 (pg/ml) | 8 hr. E1 (pg/ml) | 24 hr. E1 (pg/ml) |
| control | 564  | 543  | 745  | 482  |
| 5  | 3373 | 2236 | 3194 | 1576 |
| 6  | 4251 | 3323 | 4137 | 1804 |
| 7  | 1921 | 1839 | 2101 | 1476 |
| 9  | 1300 | 1182 | 1171 | 739  |
| 14 | 4298 | 2626 | 3179 | 1054 |
| 15 | 719  | 948  | 750  | 554  |

Control: cell lines not transfected with 17βHSD1

Example 26: Determination of the Inhibition of Human 17βHSD In Vivo

To evaluate the biological activity of compounds in vivo, measurement of decrease in the formation of E2 in the plasma of mice treated with the candidate substance 9 was used. Female mice of NMRI outbred strain aged 8 weeks were used for this purpose. These animals were treated for 7 or 14 days with compound 9 dissolved in an oil vehicle (olive oil), administered orally with a gastric gavage, once a day, 20 mg/kg of mouse weight in a total volume of 0.1 ml. Parallel control group of animals was treated with the vehicle alone. After 7 or 14 days, blood was collected for the purpose of processing blood plasma and analysis of E2 levels. In parallel, a dissection was performed and macroscopic evaluation of individual organs.

Administration of the compound was well tolerated by the animals; no significant weight loss was observed and macroscopic analysis of organs did not reveal any obvious pathology. Plasma of both treated and control animals was subjected to the of immunoenzymatic analysis for quantification of E2. This analysis showed highly significant reduction in the levels of the E2 hormone after 14 days of administration, which is consistent with the inhibition of 17βHSD in vivo (Table 6).

TABLE 6

Inhibition of E2 production after administration of compound 9 in vivo in plasma of experimental animals.

| Vehicle 7 days | E2 (pg/ml) | Vehicle 14 days | E2 (pg/ml) |
| --- | --- | --- | --- |
| Mouse B_1 | 4660 | Mouse D_1 | 5447 |
| Mouse B_2 | 4988 | Mouse D_2 | 5991 |
| Mouse B_3 | 4570 | Mouse D_3 | 4796 |
| Mouse B_4 | 6835 | Mouse D_4 | 4973 |
| Mouse B_5 | 6202 | mean value ± σ | 5302 ± 2416 |
| Mouse B_6 | 6372 | | |
| Mouse B_7 | 4824 | | |
| mean value ± σ | 5632 ± 950 | | |

| Compound 9:7 days 20 mg/kg daily | E2 (pg/ml) | Compound 9:14 days 20 mg/kg daily | E2 (pg/ml) |
| --- | --- | --- | --- |
| Mouse A_1 | 4927 | Mouse C_1 | 6020 |
| Mouse A_2 | 4357 | Mouse C_2 | 2668 |
| Mouse A_3 | 6020 | Mouse C_3 | 2657 |
| Mouse A_4 | 7379 | Mouse C_4 | 3566 |
| Mouse A_6 | 5857 | Mouse C_5 | 4312 |
| Mouse A_7 | 5617 | Mouse C_6 | 4025 |
| mean value ± σ | 5693 ± 1034 | mean value ± σ | 3874 ± 1253 |
| p | 0.362 | p | 0.019 |

P: The value of statistical significance;
σ: standard deviation

Example 27: Study of Efficacy of Compound 9 on Breast Carcinoma Tumors Initiated from T47D Cell Lines The preparation of the final formulation of compounds used, the incubation of the eggs, the administration of test compounds, the toxicity analysis and the final statistical analysis were carried out at INOVOTION, La Tronche, 38700, France.

Fertilized White Leghorn eggs were incubated at 37.5° C. with 50% relative humidity for 9 days. At this time (E9), the chorioallantoic membrane (CAM) was dropped by drilling a small hole through the eggshell into the air sac and a 1 cm² window was cut in the eggshell above the CAM. Twenty one eggs were used for each condition.

T47D cell line was cultivated in RPMI medium with 10% FBS, 1% non-essential amino acids, 1% sodium bicarbonate and 0.1 nmol·l$^{-1}$ estrone (and 1% penicillin/streptomycin). Cells (at 80% confluency, passage 28) were detached with trypsin, washed with complete medium and suspended in PBS. An inoculum was added onto the CAM of each egg (E9). Eggs were then randomized in 3 groups.

At day 10 (E10), tumors began to be detectable. They were then treated for 6 days, every day (E11, E12, E13, E14) by dropping 100 μl of vehicle (0.5% DMSO in PBS), or ref compound (4-hydoxytamoxifen), or tested compound 9 at one dose onto the tumor (see Table 7 for concentration).

TABLE 7

Groups for study

| Group description | Molecule name | Concentration |
| --- | --- | --- |
| Group 1 Negative ctrl (vehicle) | DMSO in PBS | 0.5% DMSO |
| Group 2 Positive ctrl (ref compound) | Tamoxifen | 200 μmol · l$^{-1}$ |
| Group 3 Exp. group 1 | compound 9 | 50 μmol · l$^{-1}$ |

At day 15 (E15) the upper portion of the CAM was removed, washed in PBS and then directly transferred in PFA (fixation for 48 hrs); the tumors were then carefully cut away from normal CAM tissue and weighted. A one-way ANOVA analysis with post-tests has been used for these data.

In parallel, a 1 cm² portion of the lower CAM was collected to evaluate the number of metastasis cells. Genomic DNA is extracted from the CAM and analyzed by qPCR with specific primers for Alu sequences. Statistical analysis was applied on data from the Bio-Rad CFX Manager 3.1 software.

The toxicity after 6 days of the treatment was characterized by the number of dead embryos, eventual visible macroscopic abnormalities were evaluated as well.

The target of this study was to test efficacy of compound 9 on breast carcinoma initiated from T47D cells on INOVOTION model. At day 16 of embryo development, following 4 treatments (at day 2, 3, 4 and 5 after grafting), tumors were collected, fixed, cleaned and weighted: at the dose tested (50 μmol·l$^{-1}$) compound 9 had the same effect as 4-hydoxytamoxifen, used as positive control (200 μmol·l$^{-1}$), showing a 12-13% reduction, see FIG. 2A.

Concerning metastasis, both compounds showed a reduction of metastasis, see FIG. 2B. These reduction are not statistical significant because of a large variation within the control group. T47D cell is not an invasive cell line. Therefore it is difficult to see statistical difference between untreated group (there were already just a few human cells in lower CAM) and treated groups in term of metastasis.

In term of toxicity, the same ratio of dead/alive eggs between groups was observed, even in negative control group, see FIG. 2C. No specific toxicity of compound 9 was proven.

INDUSTRIAL APPLICABILITY

Compounds of the invention may be used for diagnosis and possibly also for the treatment of estrogen dependent diseases, especially estrogen-dependent types of tumors, endometriosis, skin diseases or disorders of sexual maturation. Substances may find application in the treatment of infertility, to induce premature menopause, hormonal castration, or as contraceptives.

Estrogen-dependent diseases include breast cancer, ovarian cancer, uterine cancer, endometriosis, adenomyosis, menorrhagia, metrorrhagia, dysmenorrhea, uterine fibroids, polycystic ovarian syndrome, fibrocystic breast disease, prostate cancer, non-small cell lung cancer (NSCLC), squamous cell carcinoma, colorectal cancer, gastric cancer, acne, hirsutism, pseudohermaphroditism, seborrheic dermatitis, androgens induced alopecia, hyperestrogenism.

The invention claimed is:

1. 15β-substituted derivatives of estrone of formula I,

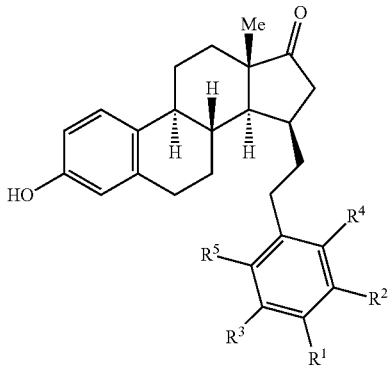

(I)

wherein:
substituents $R^1$, $R^2$, $R^3$, $R^4$, $R^5$ are independently selected from the group consisting of: $C_1$-$C_4$alkyl; $C_1$-$C_4$ alkoxy; $C_1$-$C_4$ halogenalkyl; halogen; $COOR^6$; H or OH; wherein $R^6$ is $C_1$-$C_4$alkyl;
or $R^1$ and $R^2$ together form an aryl;
and wherein the aromatic ring in position C-15 can be mono-, di-, tri-, tetra- and penta-substituted with the $R^1$ to $R^5$ substituents.

2. 15β-substituted derivatives of estrone of formula I according to claim 1, wherein $R^1$ and $R^2$ together with the phenyl on which they are bound form a naphthyl, in which case $R^3$, $R^4$ and $R^5$ are hydrogen atoms.

3. A method for preparing compounds of formula I according to claim 1, comprising the following steps:
    a) 3-(t-butyldimethylsilyloxy)-15β-vinyl-estra-1.3.5(10)-trien-17-one reacts in a cross metathesis reaction with a second olefin in the presence of a ruthenium catalyst, at temperature from 40° C. to 70° C. under inert atmosphere;
    b) t-butyldimethylsilyl protecting group of the product of the cross metathesis reaction from the previous step is removed;
    c) hydrogenation of the unsaturated deprotected product of the step b) leading to formation of the compound of formula (I);
    wherein respective second olefins in step a) are selected from styrene, vinylnaphtalene, vinylphenol, vinyl-benzene, either of which can be further substituted with halogen, alkyl, haloalkyl, alkoxy and/or acetoxy group;
    and wherein the ruthenium catalyst is selected from a group comprising Hoveyda Grubbs catalyst second generation, Hoveyda Grubbs catalyst first generation, Grubbs catalyst second generation, Grubbs catalyst first generation.

4. A method for preparing compounds of formula I according to claim 3, comprising the following steps:
    a) 3-(t-butyldimethylsilyloxy)-15β-vinyl-estra-1.3.5(10)-trien-17-one reacts in a cross metathesis reaction with a second olefin in the presence of a ruthenium catalyst, and in the presence of CuI co-catalyst, at temperature from 40° C. to 70° C. under inert atmosphere;
    b) t-butyldimethylsilyl protecting group of the product of the cross metathesis reaction from the previous step is removed using tetrabutylammonium fluoride;
    c) hydrogenation of the unsaturated deprotected product of the step b) leading to formation of the compound of formula (I);
    wherein respective second olefins in step a) are selected from styrene, vinylnaphtalene, vinylphenol, vinyl-benzene, either of which can be further substituted with halogen, alkyl, haloalkyl, alkoxy and/or acetoxy group;
    and wherein the ruthenium catalyst is selected from a group comprising Hoveyda Grubbs catalyst second generation, Hoveyda Grubbs catalyst first generation, Grubbs catalyst second generation, Grubbs catalyst first generation.

5. The method according to claim 4, characterized in that:
    in the first step, Hoveyda-Grubbs ruthenium catalyst second generation and CuI, respectively, are added to a solution of 3-(t-butyldimethylsilyloxy)-15β-vinyl-estra-1.3.5(10)-trien-17-one and the respective second olefin in a solvent mixture of $CH_2Cl_2$/trifluorotoluene in a volume ratio of 2/1 under an inert atmosphere;
    the resulting mixture is first stirred at 40-70° C. for 4-12 hr, and, subsequently, further addition of the respective second olefin and the Hoveyda-Grubbs ruthenium catalyst second generation is performed, and the reaction mixture is stirred at the same temperature overnight;
    then the reaction is quenched by evaporation of solvents, and products of cross-metathesis are obtained by chromatography on silica gel;
    in the second step, solution of TBAF in THF is successively added dropwise to the metathesis product, dissolved in THF, at room temperature; after 1 h, water is added and the reaction mixture is extracted with $CH_2Cl_2$ and/or $CHCl_3$; the combined organic phases are then washed with saturated NaCl solution, dried with $MgSO_4$; the solvents are removed under reduced pressure and deprotected products are isolated by chromatography on silica gel;
    and
    in a third step, the flask with a mixture of deprotected product of metathesis in ethyl acetate and Pd/C catalyst (10 wt. %) is evacuated under vigorous stirring, and then filled with hydrogen gas; the reaction mixture is stirred overnight, then filtered through diatomaceous earth $SiO_2$, and solvents are removed.

6. Method of diagnosing and/or treatment of estrogen-dependent diseases selected from breast cancer, ovarian cancer, uterine cancer, endometriosis, adenomyosis, menorrhagia, metrorrhagia, dysmenorrhea, uterine fibroids, polycystic ovarian syndrome, fibrocystic disease of the breast, prostate cancer, non-small cell lung cancer (NSCLC), squamous cell carcinoma, colorectal carcinoma, gastric cancer, acne, hirsutism, pseudohermaphroditism, seborrheic dermatitis, androgens induced alopecia, hyperestrogenism, comprising the step of administration of at least one 15β-substituted derivative of estrone of formula I according to claim 1.

7. Method of treatment of infertility comprising the step of administration of at least one 15β-substituted derivative of estrone of formula I according to claim 1.

8. Method of inducing of premature menopause, comprising the step of administration of at least one 15β-substituted derivative of estrone of formula I according to claim 1.

9. Method of hormonal castration, comprising the step of administration of at least one 15β-substituted derivative of estrone of formula I according to claim 1.

10. Method of contraception, comprising the step of administration of at least one 15β-substituted derivative of estrone of formula I according to claim 1.

\* \* \* \* \*